US006825352B2

(12) United States Patent
Nelson et al.

(10) Patent No.: US 6,825,352 B2
(45) Date of Patent: Nov. 30, 2004

(54) PREPARATION AND USE OF ORTHO-SULFONAMIDO ARYLHYDROXAMIC ACIDS AS MATRIX METALLOPROTEINASE INHIBITORS

(75) Inventors: Frances Christy Nelson, Wyckoff, NJ (US); Arie Zask, New York, NY (US); James Ming Chen, San Ramon, CA (US); Dominick Mobilio, Warren, NJ (US); Ramaswamy Nilakantan, Closter, NJ (US)

(73) Assignee: Wyeth, Madison, NJ (US)

(*) Notice: Subject to any disclaimer, the term of this patent is extended or adjusted under 35 U.S.C. 154(b) by 0 days.

(21) Appl. No.: 10/231,584

(22) Filed: Aug. 30, 2002

(65) Prior Publication Data

US 2003/0035332 A1 Feb. 20, 2003

Related U.S. Application Data

(62) Division of application No. 09/792,798, filed on Feb. 23, 2001, now Pat. No. 6,465,508.
(60) Provisional application No. 60/266,305, filed on Feb. 25, 2000, now abandoned.

(51) Int. Cl.[7] .................... C07D 215/16; C07D 215/38; C07D 215/20; C07D 209/02; C07D 209/04
(52) U.S. Cl. ................ 546/153; 546/155; 546/156; 546/157; 546/159; 546/162; 546/167; 546/168; 546/170; 548/483; 548/484; 548/486; 548/492; 548/494; 548/503; 548/509; 548/511
(58) Field of Search ........................ 546/153, 155, 546/156, 157, 159, 162, 167, 168, 170; 548/483, 484, 486, 492, 494, 503, 509, 511

(56) References Cited

U.S. PATENT DOCUMENTS

| 5,455,258 A | 10/1995 | MacPherson et al. |
| 5,506,242 A | 4/1996 | MacPherson et al. |
| 5,552,419 A | 9/1996 | MacPherson et al. |

FOREIGN PATENT DOCUMENTS

| EP | 0606046 A1 | 7/1994 |
| EP | 0757984 A1 | 2/1997 |
| WO | WO 95/35275 A1 | 12/1995 |
| WO | WO 95/35276 A1 | 12/1995 |
| WO | WO 96/00214 A1 | 1/1996 |
| WO | WO 96/27583 A1 | 9/1996 |
| WO | WO 97/19068 A1 | 5/1997 |
| WO | WO 97/22587 A1 | 6/1997 |
| WO | WO 97/27174 A1 | 7/1997 |
| WO | WO 98/16503 | 4/1998 |
| WO | WO 98/16514 | 4/1998 |
| WO | WO 00/44710 A3 | 8/2000 |

OTHER PUBLICATIONS

Woessner, J.F., Jr. Faseb J. 1991, 5, 2145.
MacPherson, L.J., J.Med.Chem. 1997, 40, 2525–2532.
Cawson, T.E. Pharmacol. Ther. 1996, 70, 163.
Powell, W.C., et al, Cur. Top. Microbiol. and Immunol. 1996, 213, 1.
Dean, D.D., Sem. Arthritis Rheum. 1991, 20, 2.
Ray, J.M., et al., Exp. Opin. Invest. Drugs, 1996, 5, 323.
Nuovo, G. J., et al., Cancer Res. 1995, 55, 267–275.
Walther, M. M. et al., J. Urol., 1995, 153 (Suppl. 4), 403 A.
Tokuraku, M., et al., Int. J. Cancer, 1995, 64, 355.
Himelstein, B., et al., Proc. Am. Assoc. Cancer Res. Ann. Meet. 1996, 37, 632.
Ueda, Y., et al., Am. J. Pathol. 1996, 148, 611.
Gress, T. M., et al., Int. J. Cancer 1995, 62, 407.
Kawashima, A., et al., Virchows Arch., 1994, 424, 547–552.
Dollery, C.M., et al., Circ. Res. 1995, 77, 863.
Zempo, N., et al., Arterioscler. Thromb. Vasc. Biol., 1996, 16, 28.
Lee, R. T., et al., Arterioscler. Thromb. Vasc. Biol. 1996, 16, 1070.
Sapolsky, A.I., et al., J. Clin. Invest. 1976, 58, 1030.
Pelletier, J.P., et al., Arthritis Rheum. 1983, 26, 63.
Freiji, J.M. et al., Biol. Chem. 1994, 269, 16766.
Mitchell, P.G., et al., J. Clin. Invest., 1996, 97, 761.
Reboul, P., et al., Arthritis Rheum., 1995, 38 (Suppl. 9), S268.
Shlopov, B.V., et al., Arthritis Rheum., 1995, 38 (Suppl. 9), S313.
Reboul, P., et al., J. Clin. Invest., 1996, 97 2011.
Chen, CA, 133:360381, abstract of J.Am.Chem.Soc. 122(4), 9648–9654, 2000.

*Primary Examiner*—D. Margaret Seamen
(74) *Attorney, Agent, or Firm*—Anne M. Rosenblum

(57) ABSTRACT

Ortho-sulfonamido aryl hydroxamic acids are provided which are useful, inter alia, for the inhibition of matrix metalloproteinases and the treatment of conditions associated with overexpression of MMPs.

18 Claims, No Drawings

PREPARATION AND USE OF ORTHO-SULFONAMIDO ARYLHYDROXAMIC ACIDS AS MATRIX METALLOPROTEINASE INHIBITORS

This application is a divisional of application Ser. No. 09/792,798 filed Feb. 23, 2001 now U.S. Pat. No. 6,465,508, which claims the benefit of U.S. Provisional Application 60/266,305, filed Feb. 25, 2000 now abandoned; the entire disclosure of each is hereby incorporated by reference.

BACKGROUND OF THE INVENTION

The present invention relates to novel, low molecular weight, non-peptide inhibitors of matrix metalloproteinases (e.g. gelatinases, stromelysins and collagenases) which are usefull for the treatment of diseases in which these enzymes are implicated such as arthritis, tumor metastasis, tissue ulceration, abnormal wound healing, periodontal disease, bone disease, proteinuria, aneurysmal aortic disease, degenerative cartilage loss following traumatic joint injury, demyelinating diseases of the nervous system and HIV infection.

More particularly this invention provides orthosulfonamido aryl hydroxamine acids as matrix metalloproteinase inhibitors processes for their preparation and pharmaceutical compositions containing them.

Matrix metalloproteinases (MMPs) are a group of enzymes that have been implicated in the pathological destruction of connective tissue and basement membranes [Woessner, J. F., Jr. FASEB J. 1991, 5, 2145; Birkedal-Hansen, H.; Moore, W. G. I.; Bodden, M. K.; Windsor, L. J.; Birkedal-Hansen, B.; DeCarlo, A.; Engler, J. A. Crit. Rev. Oral Biol. Med. 1993, 4, 197; Cawston, T. E. Pharmacol. Ther. 1996, 70, 163; Powell, W. C.; Matrisian, L. M. Cur. Top. Microbiol. and Immunol. 1996, 213, 1]. These zinc containing endopeptidases consist of several subsets of enzymes including collagenases, stromelysins and gelatinases. Of these classes, the gelatinases have been shown to be the MMPs most intimately involved with the growth and spread of tumors, while the collagenases have been associated with the pathogenesis of osteoarthritis [Howell, D. S.; Pelletier, J.-P. In Arthritis and Allied Conditions; McCarthy, D. J.; Koopman, W. J., Eds.; Lea and Febiger: Philadelphia, 1993; 12th Edition Vol. 2, pp. 1723; Dean, D. D. Sem. Arthritis Rheum. 1991, 20, 2; Crawford, H. C; Matrisian, L. M. Invasion Metast. 1994–95, 14, 234; Ray, J. M.; Stetler-Stevenson, W. G. Exp. Opin. Invest. Drugs, 1996, 5, 323].

It is known that the level of expression of gelatinase is elevated in malignancies, and that gelatinase can degrade the basement membrane which may lead to tumor metastasis [Powell, W. C.; Matrisian, L. M. Cur. Top. Microbiol. and Immunol. 1996, 213, 1; Crawford, H. C; Matrisian, L. M. Invasion Metast. 1994–95, 14, 234; Ray, J. M.; Stetler-Stevenson, W. G. Exp. Opin. Invest. Drugs, 1996, 5, 323; Himelstein, B. P.; Canete-Soler, R; Bernhard, E. J.; Dilks, D. W.; Muschel, R. J. Invasion Metast. 1994–95, 14, 246; Nuovo, G. J.; MacConnell, P. B.; Simsir, A.; Valea, F.; French, D. L. Cancer Res. 1995, 55, 267–275; Walther, M. M.; Levy, A.; Hurley, K.; Venzon, D.; Linehen, W. M.; Stetler-Stevenson, W. J Urol. 1995, 153 (Suppl. 4), 403A; Tokuraku, M; Sato, H.; Murakami, S.; Okada, Y.; Watanabe, Y.; Seiki, M. Int. J. Cancer, 1995, 64, 355; Himelstein, B.; Hua, J.; Bernhard, E.; Muschel, R. J. Proc. Am. Assoc. Cancer Res. Ann. Meet. 1996, 37, 632; Ueda, Y.; Imai, K.; Tsuchiya, H.; Fujimoto, N.; Nakanishi, I.; Katsuda, S.; Seiki, M.; Okada, Y. Am. J. Pathol. 1996, 148, 611; Gress, T. M.; Mueller-Pillasch, F.; Lerch, M. M.; Friess, H.; Buechler, M.; Adler, G. Int. J. Cancer, 1995, 62, 407; Kawashima, A.; Nakanishi, I.; Tsuchiya, H.; Roessner, A.; Obata, K.; Okada, Y. Virchows Arch., 1994, 424, 547–552.]. Angiogenesis, required for the growth of solid tumors, has also recently been shown to have a gelatinase component to its pathology [Crawford, H. C; Matrisian, L. M. Invasion Metast. 1994–95, 14, 234; Ray, J. M.; Stetler-Stevenson, W. G. Exp. Opin. Invest. Drugs, 1996, 5, 323.]. Furthermore, there is evidence to suggest that gelatinase is involved in plaque rupture associated with atherosclerosis [Dollery, C. M.; McEwan, J. R.; Henney, A. M. Circ. Res. 1995, 77, 863; Zempo, N.; Koyama, N.; Kenagy, R. D.; Lea, H. J.; Clowes, A. W. Arterioscler. Thromb. Vasc. Biol. 1996, 16, 28; Lee, R. T.; Schoen, F. J.; Loree, H. M.; Lark, M. W., Libby, P. Arterioscier. Thromb. Vasc. Biol. 1996, 16, 1070.]. Other conditions mediated by MMPs are restenosis, MMP-mediated osteopenias, inflammatory diseases of the central nervous system, skin aging, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, periodontal disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

The hypothesis that MMPs are important mediators of the tissue destruction that occurs in arthritis has long been considered, since it was first recognized that these enzymes are capable of degrading collagens and proteoglycans which are the major structural components of cartilage [Sapolsky, A. I.; Keiser, H.; Howell, D. S.; Woessner, J. F., Jr.; J. Clin. Invest. 1976, 58, 1030; Pelletier, J.-P.; Martel-Pelletier, J.; Howell, D. S.; Ghandur-Mnaymneh, L.; Enis, J. E.; Woessner, J. F., Jr., Arthritis Rheum. 1983, 26, 63.], and continues to develop as new MMPs are identified. For example, collagenase-3 (MMP-13) was cloned from breast cancer cells in 1994, and the first report that it could be involved in arthritis appeared in 1995 [Freiji, J. M.; Diez-Itza, I.; Balbin, M.; Sanchez, L. M.; Blasco, R.; Tolivia, J.; Lopez-Otin, C. J. Biol. Chem. 1994, 269, 16766; Flannery, C. R.; Sandy, J. D. 102–17, 41st Ann Meet. Orth. Res. Soc. Orlando, Fla. Feb. 13–16, 1995.]. Evidence is accumulating that implicates MMP-13 in the pathogenesis of arthritis. A major structural component of articular cartilage, type II collagen, is the preferred substrate for MMP-13 and this enzyme is significantly more efficient at cleaving type II collagen than the other collagenases [Knauper, V.; Lopez-Otin, C.; Smith, B.; Knight, G.; Murphy, G. J. Biol Chem., 1996, 271, 1544–1550; Mitchell, P. G.; Magna, H. A.; Reeves, L. M.; Lopresti-Morrow, L. L.; Yocum, S. A.; Rosner, P. J.; Geoghegan, K. F.; Hambor, J. E. J. Clin. Invest. 1996, 97, 761.]. MMP-13 is produced by chondrocytes, and elevated levels of MMP-13 has been found in human osteoarthritic tissues [Reboul, P.; Pelletier, J-P.; Hambor, J.; Magna, H.; Tardif, G.; Cloutier, J-M.; Martel-Pelletier, J. Arthritis Rheum. 1995, 38 (Suppl. 9), S268;Shlopov, B. V.; Mainardi, C. L.; Hasty, K. A. Arthritis Rheum. 1995, 38 (Suppl. 9), S313; Reboul, P.; Pelletier, J-P.; Tardif, G.; Cloutier, J-M.; Martel-Pelletier, J. J. Clin. Invest. 1996, 97, 2011]. Potent inhibitors of MMPs were described over 10 years ago, but the poor bioavailability of these early peptidic, substrate mimetic MMP inhibitors precluded their evaluation in animal models of arthritis. More bioavailable, non-peptidic MMP inhibitors may be preferred for the treatment of diseases mediated by MMPs.

It is expected that small molecule inhibitors of gelatinase therefore have the potential for treating a variety of disease states. While a variety of MMP inhibitors have been identified and disclosed in the literature, the vast majority of these molecules are peptidic or peptide-like compounds that may have bioavailability and pharmacokinetic problems that would limit their clinical effectiveness. Low molecular weight, potent, long-acting, orally bioavailable inhibitors of gelatinases and collagenases are therefore highly desirable for the potential chronic treatment of the above mentioned disease states. Several non-peptide, sulfur-containing hydroxamic acids have recently been disclosed and are listed below.

U.S. Pat. Nos. 5,455,258, 5,506,242 and 5,552,419, as well as European patent application EP606,046A1 and WIPO international publications WO96/00214 and WO97/22587 disclose non-peptide matrix metalloproteinase inhibitors of which the compound CGS27023A is representative. The discovery of this type of MMP inhibitor is further detailed by MacPherson, et al. in *J. Med. Chem.*, (1997),40, 2525. Additional publications disclosing sulfonamide based MMP inhibitors which are variants of the sulfonamide-hydroxamate shown below, or the analogous sulfonamide-carboxylates, are European patent application EP-757984-A1 and WIPO international publications WO95/35275, WO95/35276, WO96/27583, WO97/19068 and WO97/27174.

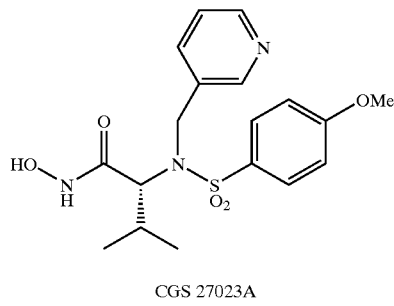

CGS 27023A

Publications disclosing β-sulfonamide-hydroxamate MMP inhibitor analogs of CGS 27023A in which the carbon alpha to the hydroxamic acid has been joined in a ring to the sulfonamide nitrogen, as shown below, include WIPO international publications WO96/33172 and WO97/20824.

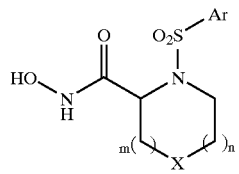

The German patent application DE19,542,189-A1 discloses additional examples of cylic sulfonamides as MMP inhibitors. In this case the sulfonamide-containing ring is fused to a phenyl ring to form an isoquinoline.

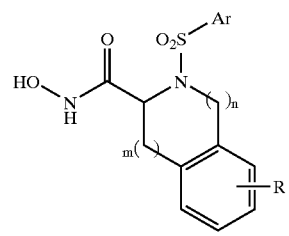

Analogs of the sulfonamide-hydroxamate MMP inhibitors in which the sulfonamide nitrogen has been replaced by a carbon atom, as shown in the general structure below, are European patent application EP-780386-A1 and WIPO international publication WO97/24117.

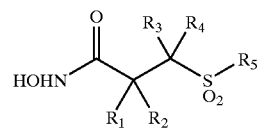

Certain ortho-sulfonamido aryl hydroxamic acids are described in U.S. Pat. No. 5,929,097, WO9816514 and WO9816520.

DESCRIPTION OF THE INVENTION

The MMP inhibiting ortho-sulfonamido aryl hydroxamic acids of the present invention are represented by formula I

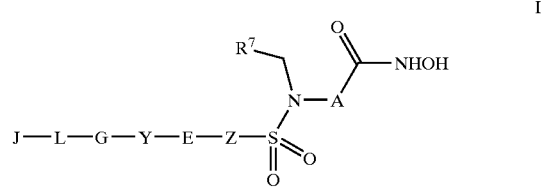

I where the hydroxamic acid moiety and the sulfonamido moiety are bonded to adjacent carbons of group A where:
A is aryl, heteroaryl or heteroaryl fused to a phenyl ring;
Z is aryl, heteroaryl, or heteroaryl fused to a phenyl;
E and G are independently $CH_2$, $NR^5$, or O, or S or a bond:
Y is cycloalkyl, cycloheteroalkyl, $-C_1-C_5$-perfluoroalkyl, alkyl, alkenyl, alkynyl, heteroalkyl, alkylaryl, or heteroaryl;
J is aryl, heteroaryl, heteroaryl fused to a phenyl, cycloalkyl, cycloheteroalkyl, $-C_1-C_5$-perfluoroalkyl, alkyl, alkenyl, or alkynyl;
$R^5$ and $R^6$ are independently H, aryl, heteroaryl, cycloalkyl, cycloheteroalkyl, $-C_1-C_4$-perfluoroalkyl, alkyl, alkenyl, or alkynyl;
$R^7$ is hydrogen, alkyl, alkenyl, alkynyl, aryl, heteroaryl, cycloalkyl or 3–6 membered cycloheteroalkyl; or
$R^7CH_2$—N—A— can form a non-aromatic 1,2-benzo-fused 7–10 membered heterocyclic ring optionally containing an additional heteroatom selected from O, S and N wherein said heterocyclic ring may be optionally fused to another benzene ring;
L is $-C(O)-$, $S(O)_y$, $-NR^5C(O)NR^6-$, $-NR^5C(O)O-$, $-OC(O)NR^5-$, $-SC(O)-$, $-C(O)S-$, $-NR^5C(O)-$, $-C(O)NR^5-$, $-SC(O)NR^5$, $-NR^5C(O)S-$, $-OC(O)O-$;

y is 1 or 2;
and the pharmaceutically acceptable salts thereof and the optical isomers and diastereomers thereof.

Preferred compounds of the invention are those wherein:

A is aryl, heteroaryl or heteroaryl fused to a phenyl ring optionally substituted by one or more of $R^1$, $R^2$, $R^3$ and $R^4$ the same or different;

Z is aryl, heteroaryl, or heteroaryl fused to a phenyl, optionally substituted by one or more of $R^{10}$, $R^{11}$, $R^{12}$ and $R^{13}$ the same or different;

$R^1$, $R^2$, $R^3$, $R^4$, $R^{10}$, $R^{11}$, $R^{12}$, $R^{13}$, $R^{14}$, $R^{15}$, $R^{16}$, $R^{17}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ are independently —H, —COR$^5$, —F, —Br, —Cl, —I, C(O)NR$^5$OR$^6$, —CN, —OR$^5$, —C$_1$–C$_4$-perfluoroalkyl, —S(O)$_x$R$^5$, —OPO(OR$^5$)OR$^6$, —PO(OR$^6$)R$^5$, —OC(O)NR$^5$R$^6$, —COOR$^5$, —CONR$^5$R$^6$, —SO$_3$H, —NR$^5$R$^6$, —NR$^5$COR$^6$, —NR$^5$COOR$^6$, —SO$_2$NR$^5$R$^6$, —NO$_2$, —N(R$^5$)SO$_2$R$^6$, NR$^5$CONR$^5$R$^6$NR$^5$C(=NR$^6$)NR$^5$R$^6$, 3–6 membered cycloheteroalkyl, aryl, heteroaryl, biphenyl, —SO$_2$NHCOR$^{18}$, —CO(NH)SO$_2$R$^{18}$, -tetrazol-5-yl, —SO$_2$NHCN, —SO$_2$NHCONR$^5$R$^6$ or straight chain or branched —C$_1$–C$_6$ alkyl, —C$_2$–C$_6$-alkenyl, or —C$_2$–C$_6$-alkynyl, or —C$_3$–C$_6$-cycloalkyl, each optionally substituted with —COR$^5$, —CN, —C$_2$–C$_6$ alkenyl, —C$_2$–C$_6$ alkynyl, —OR$^5$, —C$_1$–C$_4$-perfluoroalkyl, —S(O)$_x$R$^5$, —OC(O)NR$^5$R$^6$, —COOR$^5$, —CONR$^5$R$^6$, —SO$_3$H, —NR$^5$R$^6$, —NR$^5$COR$^6$, —NR$^5$COOR$^6$, —SO$_2$NR$^5$R$^6$, —NO$_2$, —N(R$^5$)SO$_2$R$^6$, —NR$^5$CONR$^5$R$^6$, —C$_3$–C$_6$cycloalkyl, 3–6 membered cycloheteroalkyl, aryl, heteroaryl, biphenyl, —SO$_2$NHCOR$^{18}$, —CONHSO$_2$R$^{18}$; —PO(OR$^5$)OR$^6$, —PO(OR$^6$)R$^5$, -tetrazol-5-yl, C(O)NR$^5$OR$^6$, —NR$^5$C(=NR$^6$)NR$^5$R$^6$,—SO$_2$NHCONR$^5$R$^6$ or —SO$_2$NHCN; or when any of $R^1$ and $R^2$, or $R^{10}$ and $R^{11}$ or $R^{14}$ and $R^{15}$ are on adjacent carbons of A or J or Z respectively, then each pair of $R^1$ and $R^2$, or $R^{10}$ and $R^{11}$ or $R^{14}$ and $R^{15}$ together with the carbons to which they are attached can form a 5 to 7 membered saturated or unsaturated heterocyclic ring, a 5–6 membered heteroaryl ring, or a 5 to 7 membered saturated or unsaturated carbocyclic ring;

x is 0–2;

E and G are independently CH$_2$, NR$^5$, or O, or S or a bond:

Y is —C$_3$–C$_6$-cycloalkyl, —C$_3$–C$_6$-cycloheteroalkyl, —C$_1$–C$_5$-perfluoroalkyl, straight chain or branched —C$_1$–C$_6$ alkyl, straight or branched chain —C$_2$–C$_6$-alkenyl, or straight or branched chain C$_2$–C$_6$-alkynyl or heteroalkyl, alkylaryl, heteroaryl optionally substituted with $R^{20}$, $R^{21}$, $R^{22}$, and $R^{23}$;

J is aryl, heteroaryl, or heteroaryl fused to a phenyl; optionally substituted with $R^{14}$, $R^{15}$, $R^{16}$, and $R^{17}$ or —C$_3$–C$_6$-cycloalkyl, —C$_3$–C$_6$-cycloheteroalkyl, —C$_1$–C$_5$-perfluoroalkyl, straight chain or branched —C$_1$–C$_6$ alkyl, straight or branched chain —C$_2$–C$_6$-alkenyl, or straight or branched chain C$_2$–C$_6$-alkynyl;

$R^5$ and $R^6$ are independently H, aryl, heteroaryl, —C$_3$–C$_6$-cycloalkyl, —C$_3$–C$_6$-cycloheteroalkyl, —C$_1$–C$_4$-perfluoroalkyl, or straight chain or branched —C$_1$–C$_6$ alkyl, —C$_2$–C$_6$-alkenyl, or —C$_2$–C$_6$-alkynyl, each optionally substituted with —OH, —COR$^8$, —CN, —C(O)NR$^8$OR$^9$, —C$_2$–C$_6$-alkenyl, —C$_2$–C$_6$-alkynyl, —OR$^8$, —C$_1$–C$_4$-perfluoroalkyl, —S(O)$_x$R$^8$, —OPO(OR$^8$)OR$^9$, —PO(OR$^8$)R$^9$, —OC(O)NR$^8$R$^9$, —COOR$^8$, —CONR$^8$R$^9$, —SO$_3$H, —NR$^8$R$^9$,—NCOR$^8$R$^9$, —NR$^8$COOR$^9$, —SO$_2$NR$^8$R$^9$, —NO$_2$, —N(R$^8$)SO$_2$R$^9$, —NR$^8$CONR$^8$R$^9$, —C$_3$–C$_6$ cycloalkyl, 3–6 membered cycloheteroalkyl, aryl, heteroaryl, —SO$_2$NHCOR$^{19}$, —CONHSO$_2$R$^{19}$, -tetrazol-5-yl, NR$^8$C(=NR$^9$)NR$^8$R$^9$, —SO$_2$NHCONR$^8$R$^9$, or —SO$_2$NHCN;

$R^7$ is hydrogen, straight chain or branched —C$_1$–C$_6$-alkyl, —C$_2$–C$_6$-alkenyl, or —C$_2$–C$_6$-alkynyl each optionally substituted with —OH, —COR$^5$, —CN, —C$_2$–C$_6$-alkenyl, —C$_2$–C$_6$-alkynyl, —OR$^5$, —C$_1$–C$_4$-perfluoroalkyl, —S(O)$_x$R$^5$, OPO(OR$^5$)OR$^6$, —PO(OR$^5$)R$^6$, —OC(O)NR$^5$R$^6$, —COOR$^5$, —CONR$^5$R$^6$, —SO$_3$H, —NR$^5$R$^6$, —NR$^5$COR$^6$, —NR$^5$COOR$^6$, —SO$_2$NR$^5$R$^6$, —NO$_2$, —N(R$^5$)SO$_2$R$^6$, —NR$^5$CONR$^5$R$^6$, —C$_3$–C$_6$ cycloalkyl, —C$_3$–C$_6$-cycloheteroalkyl, -aryl, heteroaryl, —SO$_2$NHCOR$^{32}$, —CONHSO$_2$R$^{32}$, -tetrazol-5-yl, —NR$^5$C(=NR6)NR$^5$R$^6$, —C(O)NR$^5$OR$^6$, —SO$_2$NHCONR$^5$R$^6$ or —SO$_2$NHCN;

or $R^7$ is phenyl or naphthyl, optionally substituted by $R^{24}$, $R^{25}$, $R^{26}$ and $R^{27}$ or a 5 to 6 membered heteroaryl group optionally substituted by $R^{28}$, $R^{29}$, $R^{30}$ and $R^3$; or $R^7$ is C$_3$–C$_6$ cycloalkyl or 3–6 membered cycloheteroalkyl; or $R^7$CH$_2$—N—A— (where $R^7$ is bonded to A) can form a non-aromatic 1,2-benzo-fused 7–10 membered heterocyclic ring optionally containing an additional heteroatom selected from O, S and N wherein said heterocyclic ring may be optionally fused to another benzene ring such as for example:

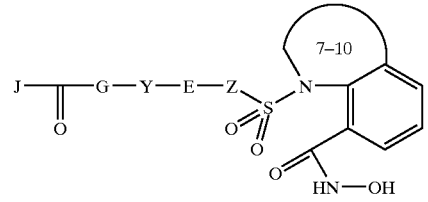

or (fused):

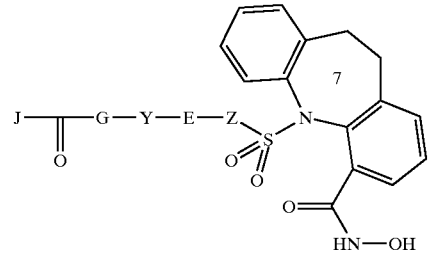

$R^8$ and $R^9$ are independently H, aryl or heteroaryl, —C$_3$–C$_7$ cycloalkyl or 3 to 6 membered cycloheteroalkyl, —C$_1$–C$_4$-perfluoroalkyl, straight chain or branched —C$_1$–C$_6$-alkyl, —C$_2$–C$_6$-alkenyl, or —C$_2$–C$_6$-alkynyl, each optionally substituted with hydroxy, alkoxy, aryloxy, —C$_1$–C$_4$-perfluoroalkyl, amino, mono- and di-C$_1$–C$_6$-alkylamino, carboxylic acid, carboalkoxy and carboaryloxy, nitro, cyano, carboxamido primary, mono- and di-C$_1$–C$_6$-alkylcarbamoyl;

$R^{18}$ and $R^{32}$ are independently aryl, heteroaryl, —C$_3$–C$_6$-cycloalkyl, —C$_3$–C$_6$-cycloheteroalkyl, —C$_1$–C$_4$-perfluoroalkyl, or straight chain or branched —C$_1$–C$_6$ alkyl, —C$_2$–C$_6$-alkenyl, or —C$_2$–C$_6$-alkynyl, each optionally substituted with —OH, —COR$^8$, —CN, —C(O)NR$^8$OR$^9$, —C$_2$–C$_6$-alkenyl, —C$_2$–C$_6$-alkynyl, —OR$^8$, —C$_1$–C$_4$-perfluoroalkyl, —S(O)$_x$R$^8$, —OPO(OR$^8$)OR$^9$, —PO(OR$^8$)R$^9$, —OC(O)NR$^8$R$^9$, —COOR$^8$, —CONR$^8$R$^9$, —SO$_3$H, —NR$^8$R$^9$,—NCOR$^8$R$^9$, —NR$^8$COOR$^9$, —SO$_2$NR$^8$R$^9$, —NO$_2$, —N(R$^8$)SO$_2$R$^9$, —NR$^8$CONR$^8$R$^9$, cycloalkyl, 3–6 membered cycloheteroalkyl, aryl, heteroaryl, —SO$_2$NHCOR$^{19}$, —CONHSO$_2$R$^{19}$, -tetrazol-5-yl, NR$^8$C(=NR$^9$)NR$^8$R$^9$, —SO$_2$NHCONR$^8$R$^9$, or —SO$_2$NHCN;

R¹⁹ is aryl or heteroaryl, —$C_3$–$C_7$cycloalkyl or 3 to 6 membered cycloheteroalkyl, —$C_1$–$C_4$-perfluoroalkyl, straight chain or branched —$C_1$–$C_6$-alkyl, —$C_2$–$C_6$-alkenyl, or —$C_2$–$C_6$-alkynyl, each optionally substituted with hydroxy, alkoxy, aryloxy, —$C_1$–$C_4$-perfluoroalkyl, amino, mono- and di-$C_1$–$C_6$-alkylamino, carboxylic acid, carboalkoxy and carboaryloxy, nitro, cyano, carboxamido primary, mono- and di-$C_1$–$C_6$-alkylcarbamoyl;

L is —C(O)—, S(O)$_y$, —NR⁵C(O)NR⁶—, —NR⁵C(O)O—, —OC(O)NR⁵—, —SC(O)—, —C(O)S—, —NR⁵C(O)—, —C(O)NR⁵—, —SC(O)NR⁵, —NR⁵C(O)S—, —OC(O)O—;

y is 1 or 2;

and the pharmaceutically acceptable salts thereof and the optical isomers and diastereomers thereof.

It is preferred in some embodiments of the invention that both of the carbons of A adjacent to the carbon bearing the sulfonamido group have a substituent other than hydrogen.

Examples of A are phenyl optionally substituted by $C_1$–$C_6$ straight or branched chain alkyl.

Examples of Z are phenyl, e.g. where E is para to the —SO$_2$— group.

In accordance with some preferred embodiments of the present invention, E and G are independently selected from NH, O and S. In other preferred embodiments of the present invention E is O and G is NH.

In other preferred embodiments Y is $C_1$–$C_6$ straight chain alkyl, and more preferably $C_2$–$C_3$ straight chain alkyl.

In some embodiments of the present invention E and G are independently selected from CH$_2$, NH, O and S and Y is —$C_1$–$C_4$-perfluoroalkyl, or straight chain or branched —$C_1$–$C_6$ alkyl, —$C_2$–$C_6$-alkenyl, or $C_2$–$C_6$-alkynyl.

In still other embodiments of the present invention, E and G are independently selected from CH$_2$, NH, O and S and Y is straight chain or branched —$C_1$–$C_6$ alkyl.

When G is CH$_2$, in some embodiments of the invention, it is preferred that Y is —$C_2$–$C_5$ -perfluoroalkyl, or straight chain or branched —$C_1$ –$C_6$ alkyl, In still other embodiments of the present invention, E and G are CH$_2$, and Y is straight chain or branched —$C_1$–$C_6$ alkyl, and more preferably Y is straight chain or branched —$C_1$–$C_5$ alkyl.

J is preferably heteroaryl fused to a phenyl and particularly preferred is where J is benzofuranyl, benzothienyl and quinolinyl J may be indolyl.

When R¹⁴ and R¹⁵ are on adjacent atoms of J, R¹⁴, R¹⁵ and J may together preferably form a bicyclic oxygen containing aryl moiety such as benzodioxanyl or benzodioxlyl.

Preferred compounds of the present invention include:

Quinoline-2-carboxylic acid (2-{4-[(2-hydroxycarbamoyl-6-methyl-phenyl)-methyl-sulfamoyl]-phenoxy}-ethyl)-amide Benzofuran-2-carboxylic acid (3-{4-[(2-hydroxycarbamoyl-6-methyl-phenyl)-methyl-sulfamoyl]-phenoxy}-propyl)-amide Benzofuran-2-carboxylic acid (4-{4-[(2-hydroxycarbamoyl-6-methyl-phenyl)-methyl-sulfamoyl]-phenoxy}-butyl)-amide 1H-Indole-2-carboxylic acid (3-{4-[(2-hydroxycarbamoyl-6-methyl-phenyl)-methyl-sulfamoyl]-phenoxy}-propyl)-amide Benzo[b]thiophene-2 carboxylic acid (2-{4-[(2-hydroxycarbamoyl-6-methyl-phenyl)-methyl-sulfamoyl]-phenoxy}-ethyl)-amide N-{3-[4-({2-[(Hydroxyamino)carbonyl]-6-dimethylanilino}sulfonyl)-phenoxy]propyl}-1,3-benzodioxole-5-carboxamide N-{4-[4-({2-[(Hydroxyamino)carbonyl]-6-dimethylanilino}sulfonyl)-phenoxyl]butyl}-1,3-benzodioxole-5-carboxamide N-{3-[4-({2-[(Hydroxyamino)carbonyl]-6-dimethylanilino}-sulfonyl)-phenoxy]propyl}-1-benzothiophene-2-carboxamide Benzofuran-2-carboxylic acid (2-{4-[benzyl-(2-hydroxycarbamoyl-4,6dimethyl-phenyl)-sulfamoyl]-phenoxy}-ethyl)-amide.

Halogen, as used herein means fluoro, chloro, bromo and iodo.

Alkyl as used herein means a branched or straight chain radical having from 1 to 20 carbon atoms optionally substituted with one or more groups selected from halogen, cyano, nitro, hydroxy, sulfhydryl, amino, alkylamino, dialkylamino, alkoxy, aryloxy, thioalkyl, thioaryl, acyl, aroyl, acyloxy, acylamino, carboxy, carboxyalkyl, carboxyaryl, carboxamido, carboxamidoalkyl, carboxamidodialkyl, alkylsulfonamido, arylsulfonamido, aryl, heteroaryl, and more preferably from 1 to 6 carbon atoms also optionally substituted. Exemplary alkyl groups include but are not limited to methyl, ethyl, propyl, isopropyl, butyl, isobutyl, t-butyl, pentyl and hexyl also optionally substituted as well as perfluoroalkyl.

Alkenyl as used herein means a branched or straight chain radical having from 2 to 20 carbon atoms optionally substituted with one or more groups selected from halogen, cyano, nitro, hydroxy, sulfhydryl, amino, alkylamino, dialkylamino, alkoxy, aryloxy, thioalkyl, thioaryl, acyl, aroyl, acyloxy, acylamino, carboxy, carboxyalkyl, carboxyaryl, carboxamido, carboxamidoalkyl, carboxamnidodialkyl, alkylsulfonamido, arylsulfonamido, aryl, heteroaryl, and more preferably from 2 to 6 carbon atoms, with the chain containing at least one carbon-carbon double bond. Alkenyl, may be used synonymously with the term olefin and includes alkylidenes. Exemplary alkenyl groups include but are not limited to ethylene, propylene and isobutylene.

Alkynyl as used herein means a branched or straight chain radical having from 2 to 20 carbon atoms optionally substituted with one or more groups selected from halogen, cyano, nitro, hydroxy, sulfhydryl, amino, alkylamino, dialkylamino, alkoxy, aryloxy, thioalkyl, thioaryl, acyl, aroyl, acyloxy, acylamino, carboxy, carboxyalkyl, carboxyaryl, carboxamido, carboxamidoalkyl, carboxamidodialkyl, alkylsulfonamido, arylsulfonamido, aryl, heteroaryl, and more preferably from 3 to 10 carbon atoms, with the chain containing at least one carbon-carbon triple bond.

Alkoxy as used herein means an alkyl-O— group in which the alkyl group is as previously described. Exemplary alkoxy groups include but are not limited to methoxy, ethoxy, n-propoxy, i-propoxy, n-butoxy, and t-butoxy.

Aryl as used herein refers to phenyl or naphthyl which may be optionally substituted as described above (e.g. $R^{1-4}$, $R^{10-13}$, $R^{14-17}$ etc.,) such as with one to four substituents selected from the group of alkyl, halogen, cyano, nitro, hydroxy, sulfhydryl, amino, alkylamino, dialkylamino, alkoxy, aryloxy, thioalkyl, thioaryl, acyl, aroyl, acyloxy, acylamino, carboxy, carboxyalkyl, carboxyaryl, carboxamido, carboxamidoalkyl, carboxamidodialkyl, alkylsulfonamido, arylsulfonamido, aryl, or heteroaryl.

Heteroaryl, as used herein refers to a 5–6 membered heteroaromatic ring having from 1 to 3 heteroatoms independently selected from N, NH, O and S. Heteroaryl may be optionally substituted with substituents as described above (e.g. $R^{1-4}$, $R^{10-13}$, $R^{14-17}$) such as selected from the group halogen, cyano, nitro, hydroxy, sulfhydryl, amino, alkylamino, dialkylamino, alkoxy, aryloxy, thioalkyl, thioaryl, acyl, aroyl, acyloxy, acylamino, carboxy, carboxyalkyl, carboxyaryl, carboxamido, carboxamidoalkyl, carboxamidodoalkyl, alkylsulfonamido, arylsulfonamido, aryl, and heteroaryl. Heteroaryl includes, but is not limited to pyrrole, furan, thiophene, pyridine, pyrimidine, pyridazine, pyrazine, triazole, pyrazole, imidazole, isothiazole, thiazole, isoxazole and oxazole.

Cycloalkyl or saturated or unsaturated carbocyclic ring, refers to a cyclic alkyl group having from 3 to 7 carbon atoms and may include from 1 to 2 double bonds. Cycloalkyl groups may be optionally substituted.

Cycloheteroalkyl, as used herein refers to 3 to 7 membered saturated or unsaturated heterocyclic ring having one to three heteroatoms independently selected from N, NH, O, and S and optionally having 1 or 2 double bonds. Cycloheteroalkyl groups may be optionally substituted with from one to three groups. The term heterocycloalkyl or heterocyclic ring includes, but is not limited to oxazolidine, thiazolidine, imidazolidine, tetrahydrofuran, tetrahydrothiophene, tetramethylene sulfone, dihydropyran, tetrahydropyran, piperidine, pyrrolidine, dioxane, morpholine, azepine and diazepine.

The term "heteroaryl fused to a phenyl" includes, but is not limited to, benzoxazole, benzoisoxazole, indole, isoindole, benzothiophene, benzofuran, quinoline, quinazoline, quinoxaline, benzotriazole, benzimidazole, benzthiazole, benzopyrazole and isoquinoline. Substitutions may occur on one or both rings.

Pharmaceutical acceptable salts are encompassed by the present invention and include, as appropriate, inorganic and organic salts. Exemplary acid salts include, but are not limited to acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Other compounds that are acids can also form salts with alkali metals or alkali earth metals, such as sodium, potassium, calcium, or magnesium, or with organic bases or basic quaternary ammonium salts.

The compounds according to the invention can be in various stereoisomeric forms such as enantiomers or diastereomers. The invention includes optically pure forms of compounds of the present invention prepared in accordance with known methods.

The following compounds (1–10) which may be used in preparing invention compounds are known and references are given hereinbelow.

1

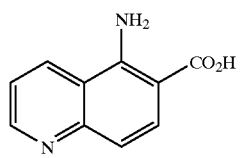

2

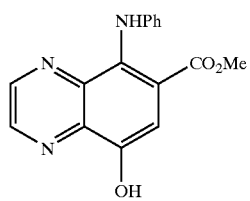

3

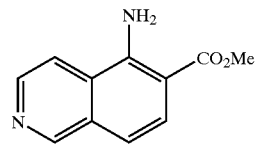

4

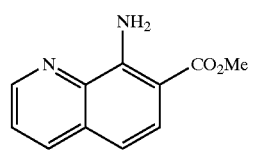

5

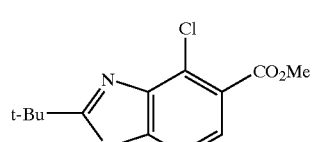

6

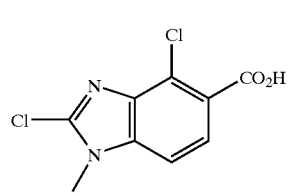

7

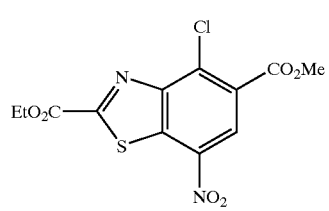

8

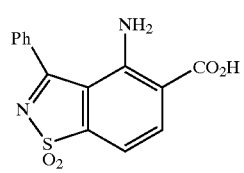

9

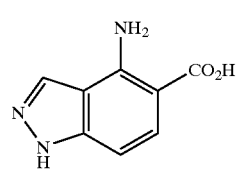

10

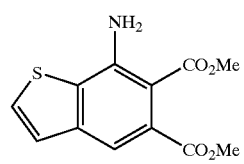

compound 1:
Meyer, Michael D.; Altenbach, Robert J.; Basha, Fatima Z.; Carroll, William A.; Drizin, Irene; Elmore, Steven W.; Kerwin, Jr James F.; Lebold, Suzanne A.; Lee, Edmund L.; Sippy, Kevin B.; Tietje, Karin R.; Wendt, Michael D. Tricyclic subsituted hexahydrobenz[e]isoindole alpha-1 adrenergic antagonists. U.S. Pat. No. 5,597,823. CAN 126:199575.
Meyer, Michael D.; Altenbach, Robert J.; Basha, Fatima Z.; Carroll, William A.; Drizin, Irene; Kerwin, James F., Jr.; Lebold, Suzanne A.; Lee, Edmund L.; Elmore, Steven W.;

et al. Preparation of tricyclic substituted benz[e]isoindoles as al adrenergic antagonists. PCT Int. Appl WO 9622992 A1 CAN 125:221858.

Compound 2:
Troll, Theodor; Schmid, Klaus. Preparation and reactions of a 2H-pyrrolo[3,4-b]pyridine and a 2H-pyrrolo[3,4-b]pyrazine. J. Heterocycl. Chem. (1986), 23(6), 1641–4.

Compound 3:
Meyer, Michael D.; Altenbach, Robert J.; Basha, Fatima Z.; Carroll, William A.; Drizin, Irene; Elmore, Steven W.; Kerwin, Jr. James F.; Lebold, Suzanne A.; Lee, Edmund L.; Sippy, Kevin B.; Tietje, Karin R.; Wendt, Michael D. Tricyclic substituted hexahydrobenz[e]isoindole alpha-1 adrenergic antagonists. U.S. Pat. No. 5,597,823. CAN 126:199575.

Compound 4:
a) Meyer, Michael D.; Altenbach, Robert J.; Basha, Fatima Z.; Carroll, William A.; Drizin, Irene; Elmore, Steven W.; Kerwin, Jr James F.; Lebold, Suzanne A.; Lee, Edmund L.; Sippy, Kevin B.; Tietje, Karin R.; Wendt, Michael D. Tricyclic substituted hexahydrobenz[e]isoindole alpha-1 adrenergic antagonists. U.S. Pat. No. 5,597,823. CAN 126:199575.
b) Meyer, Michael D.; Altenbach, Robert J.; Basha, Fatima Z.; Carroll, William A.; Drizin, Irene; Kerwin, James F., Jr.; Lebold, Suzanne A.; Lee, Edmund L.; Elmore, Steven W.; et al. Preparation of tricyclic substituted benz[e]isoindoles as a1 adrenergic antagonists. PCT Int. Appl. WO 9622992 A1 CAN 125:221858.

Compound 5:
Geach, Neil, Hawkins, David William; Pearson, Christopher John; Smith, Philip Henry Gaunt; White, Nicolas. Preparation of isoxazoles as herbicides. Eur. Pat. Appl. EP 636622 A1 CAN 122:290845.

Compound 6:
Kotovskaya, S. K.; Mokrushina, G. A.; Suetina, T. A.; Chupakhin, O. N.; Zinchenko, E. Ya.; Lesovaya, Z. I.; Mezentsev, A. S.; Chernyshov, A. I.; Samoilova, L. N. Benzimidazolyl derivatives of penicillin and cephalosporin: synthesis and antimicrobial activity. Khim.-Farm. Zh (1989), 23(8), 952–6.

Compound 7:
Wagner, Klaus. Bactericidal and fingicidal 4-chlorobenzothiazoles. Ger. Offen. DE 2136924 CAN 78:111293.

Compound 8:
Eggensperger, Heinz; Diehl, Karl H.; Kloss, Wilfried. 2-Hydroxy-4-alkoxybenzophenones. Ger. DE 1768599 711223. CAN 76:85557.

Compound 9:
Lichtenthaler, Frieder W.; Moser, Alfred. Nucleosides. 44. Benzo-separated pyrazolopyrimidines: expeditious syntheses of [3,4-g]- and [3,4-h]-linked pyrazoloquinazolinones. Tetrahedron Lett. (1981), 22(44), 4397–400.

Compound 10:
Terpstra, Jan W.; Van Leusen, Albert M. A new synthesis of benzo[b]thiophenes and benzo[c]thiophenes by annulation of disubstituted thiophenes. J. Org. Chem. (1986), 51(2), 230–8.

The invention compounds may be prepared using conventional techniques known to those skilled in the art of organic synthesis.

Accordingly this invention provides a process for preparing a compound of Formula I as defined above which comprises one of the following:

a) reacting a compound of formula II:

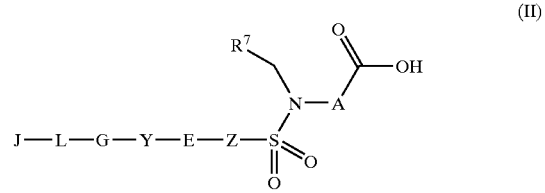

wherein J, L, G, Y, E, Z, A and $R^7$ are defined above or a reactive derivative thereof, with a compound of formula III:

to give a corresponding compound of formula I;

b) resolving a mixture (e.g. racemate) of optically active isomers of a compound of formula I to isolate one enantiomer or diastereomer substantially free of the other enantiomer or diastereomers;

c) acidifying a basic compound of formula I with a pharmaceutically acceptable acid to give a pharmaceutically acceptable salt.

Means of coupling the carboxylic acid moiety to hydroxylarnine are well known to those skilled in the art.

The following schemes (Scheme I and II) illustrates the general reaction sequence employed. For purposes of illustration only, wherein the group A is a phenyl, methyl anthranilate is reacted with p-fluorobenzenesulfonyl chloride to provide the requisite N-aryl sulfonamido-ester which is then alkylated to provide the N,N-disubstituted sulfonamide. This compound can then be converted into the elongated sulfonamide by two routes. The N,N-disubstituted sulfonamide ester may be hydrolyzed to the carboxylic acid and then subjected to a nucleophilic displacement of the fluoro substituent, or it can be treated directly with a suitable nucleophile and subsequently hydrolyzed to the acid. The acid may then be converted into the corresponding hydroxamic acid.

Scheme I

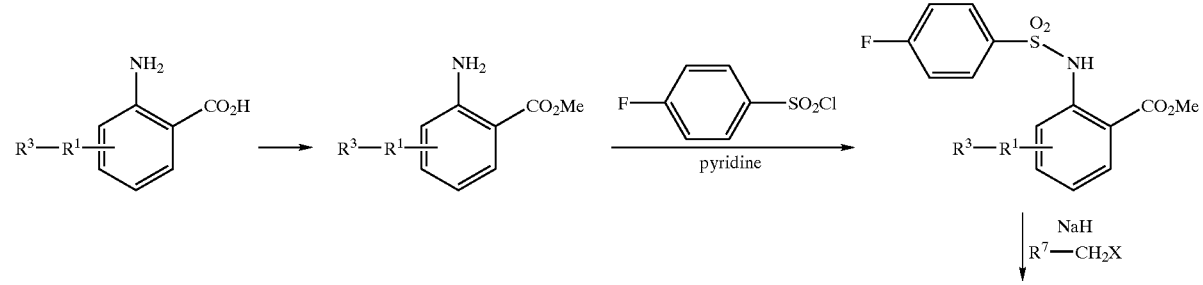

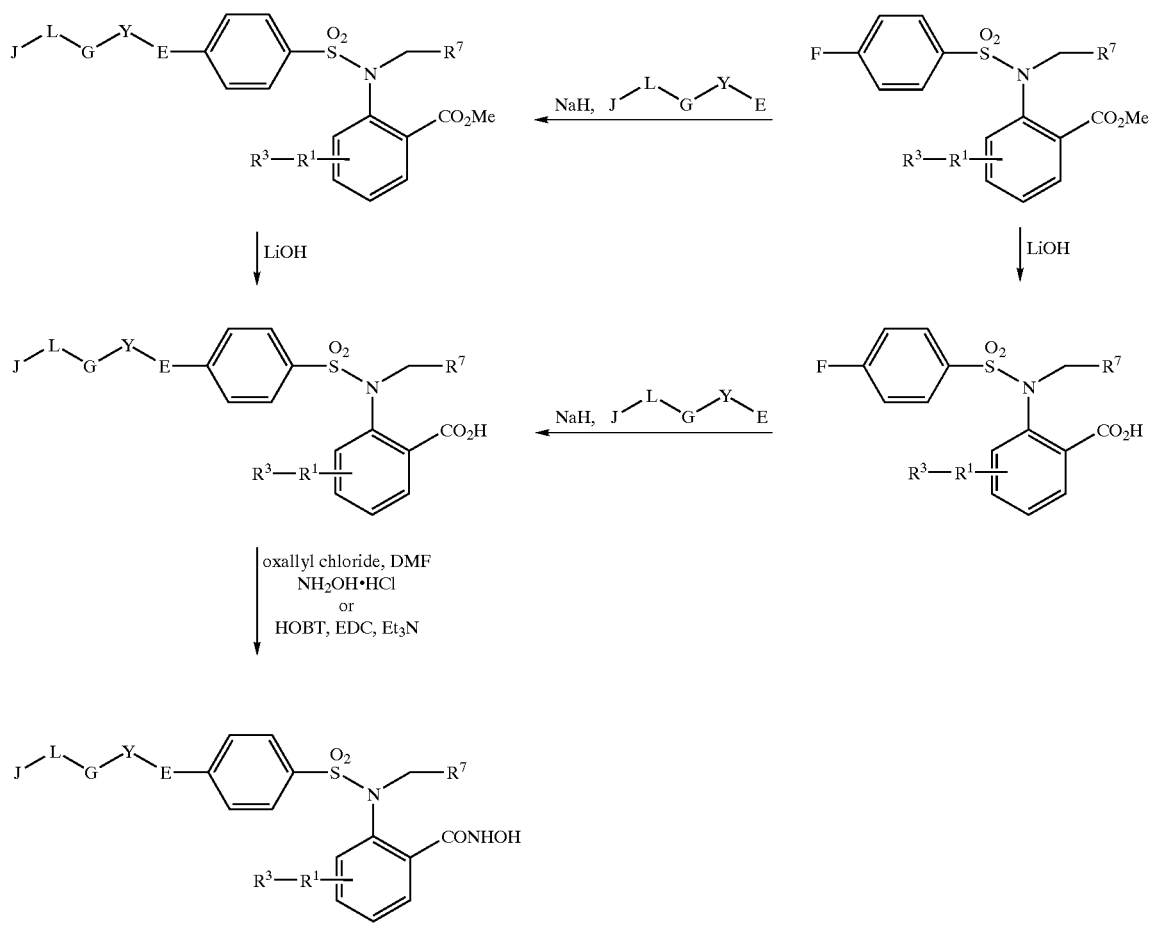

Scheme II depicts the preparation of suitable nucleophiles (for when E and G are independently N, O, or S and L is —C(O)—O or S(O)x) employed in the displacement of the aryl fluoride.

Scheme II

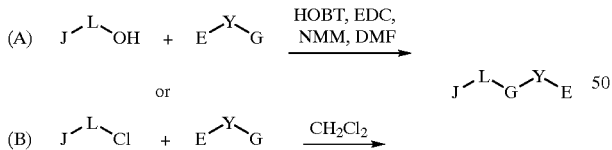

Alternatively, other nucleophiles for use in the displacement reaction (G is C) can be prepared via the route in Scheme III. A suitable ester is condensed with a lactone to provide a β-ketolactone. This lactone is then ring opened with concomitant decarboxylation to provide the requisite nucleophile for use in the displacement reaction.

Scheme III

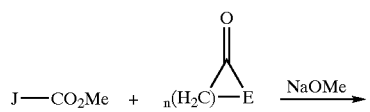

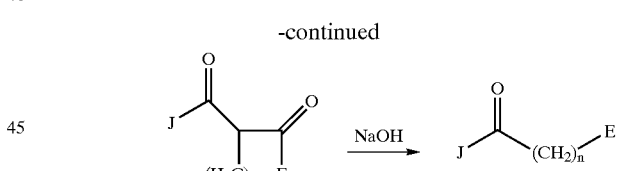

Alternatively, other compounds of the invention can be prepared via the route shown in Scheme 4. For purposes of illustration only, wherein the group A is shown as a phenyl, methyl anthranilate is reacted with pbromobenzenesulfonyl chloride to provide the requisite N-aryl sulfonamido-ester which is then alkylated to provide the N,N-disubstituted sulfonamide. This compound can then be converted into the elongated sulfonamide by two routes. The N,N-disubstituted sulfonamide ester may be hydrolyzed to the carboxylic acid and then subjected to a palladium catalyzed coupling to a suitable alkyl boron reagent (compound A, prepared via the route depicted in Scheme 5), or it can be treated directly with a suitable alkyl boron reagent and subsequently hydrolyzed to the acid. The acid may then be converted into the corresponding hydroxamic acid.

Scheme 4

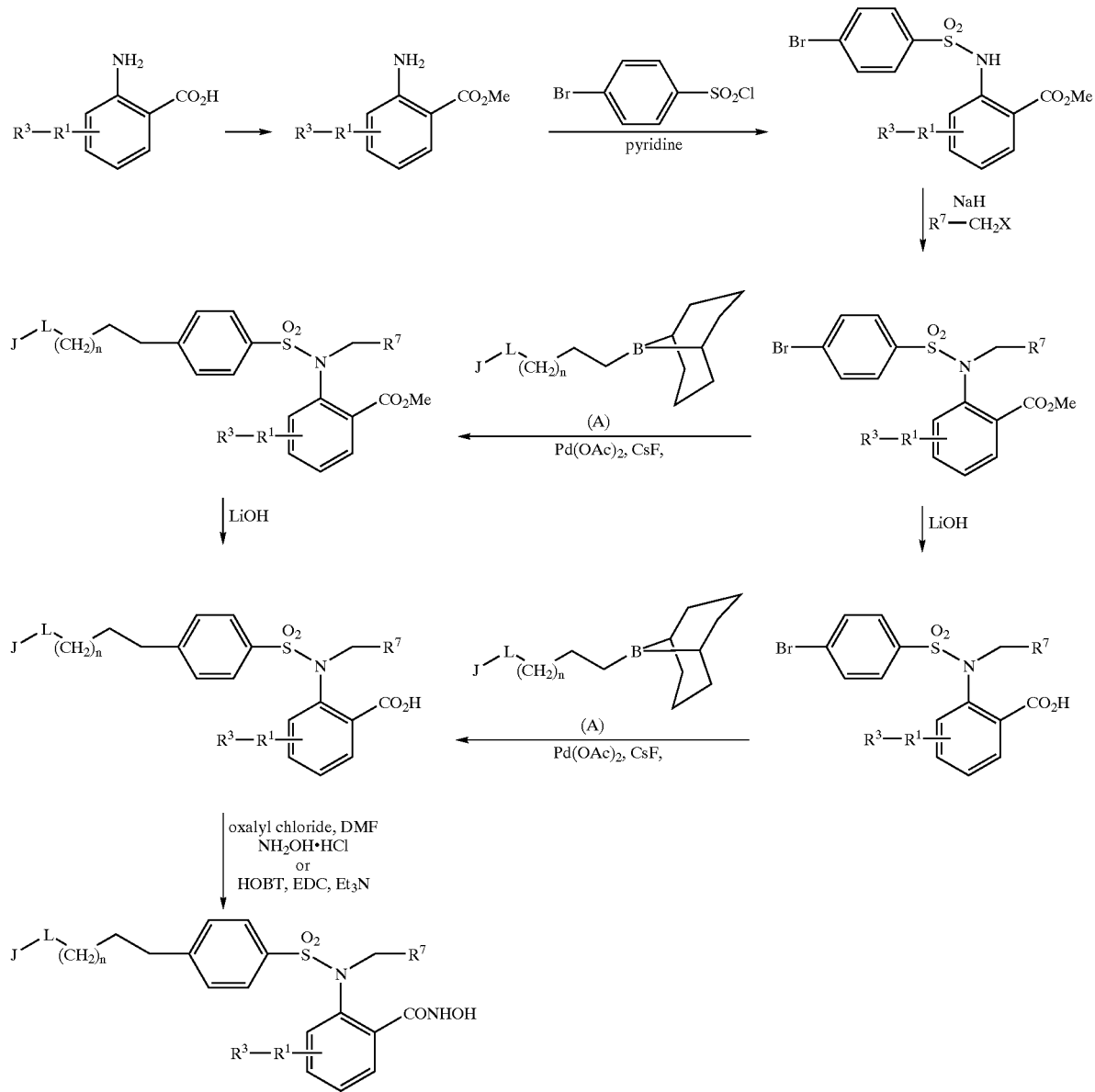

Compound A (where L is —C(O)—) may be prepared via the following route. A precursor carboxylic acid is converted to the Weinreb amide via formation of the acid chloride and subsequent displacement with methoxymethyl amine. The amide is then treated with a grignard reagent, the olefin of which is subsequently hydroborated with 9-BBN for use in the palladium coupling reaction.

Scheme 5

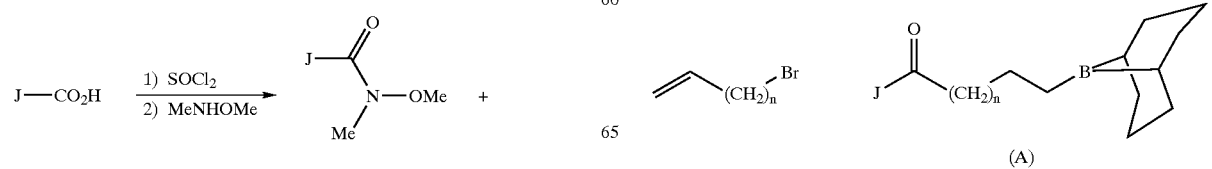

-continued

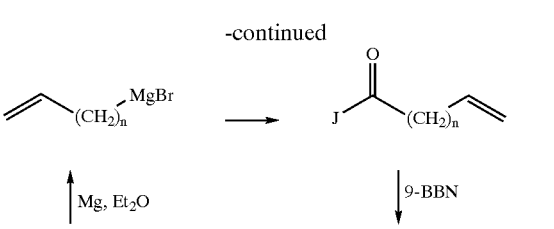

In another aspect of the present invention, the invention includes a method of treating a pathological condition or disorder mediated by matrix metalloproteinases in mammals which comprises providing to a manual in need thereof a therapeutically effective amount of a matrix metalloproteinase inhibiting compound In preferred embodiments of the invention, compounds of the present invention are particularly useful for the treatment of rheumatoid arthritis, tumor metastasis, tissue ulceration, abnormal wound healing, periodontal disease, bone disease and HIV infection.

Compounds of this invention may be provided to a patient in need thereof. They may be administered neat or with a pharmaceutical carrier to the patient or provided in the form of a pro-drug which will be converted by the patient. The pharmaceutical carrier may be solid or liquid and generally may be any pharmaceutically acceptable carrier. Formulation of drugs is discussed, for example, in Hoover, J. E., *Remington's Pharameutical Sciences*, Mack Publishing Company, Easton, Pa. 1975.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering from a disease or condition in which MMPs and TACE are involved must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

The following specific examples are included for illustrative purposes and are not to be construed as limiting to this disclosure in any way. Other procedures useful for the preparation of the compounds of this invention will be apparent to those skilled in the art of synthetic organic chemistry.

EXAMPLE 1

Methyl 2-[[(4-fluorophenyl)sulfonyl](methyl)amino] 3-methyl benzoate

Methyl 2-[[(4-fluorophenyl)sulfonyl]amino]3-methyl benzoate (3.0 g, 9.3 mmol) was dissolved in dimethylformamide (DMF) (30 ml) and cooled to 0° C. Iodomethane (0.75 ml, 12.0 mmol) was added, followed by sodium hydride (0.4 g, 11 mmol, 60% dispersion in mineral oil) and the reaction was allowed to warm to room temperature. After 15 hours, the reaction was diluted with water and extracted 3 times with ethyl acetate. The organics were combined, washed with brine, dried over $MgSO_4$, and concentrated in vacuo to provide 2.8 g (90%) of the N-methyl sulfonamide as a white solid. $^1$H NMR (DMSO-$d_6$): δ 2.0 (s, CH3), 3.25 (s, CH3), 3.55 (s, CH3), 7.1–7.57 (m, 5 Ar H), 7.69–7.73 (m, 2 Ar H). Electrospray Mass Spec: M/z 338.3 (M+H)$^+$.

EXAMPLE 2

Methyl 2-[[(4-fluorophenyl)sulfonyl](methyl)amino] 3-methyl benzoic acid

The product of Example 1 (2.8 g, 8.3 mmol) and 0.4 g lithium hydroxide (LiOH) were added to 65 ml of a (1:1.5:1)

mixture of tetrahydrofuran (THF):methanol (MeOH):water, and stirred at room temperature. After 15 hours, the solution was neutralized with 1N HCl and extracted 3 times with dichloromethane (CH$_2$Cl$_2$). The organics were combined, washed with brine, dried over MgSO$_4$, and concentrated in vacuo to provide 2.56 g (95%) of the carboxylic acid as a white solid. $^1$H NMR (DMSO-d$_6$): δ 1.9 (s, CH3), 3.20 (s, CH3), 7.35–7.46 (m, 4 Ar H) 7.55–7.58 (d, 1 Ar H), 7.69–7.74 (m, 2 Ar H). Electrospray Mass Spec: m/z 322.2 (M–H)$^+$.

EXAMPLE 3

3-Methyl-2-[methyl[(4-[2-[(2-quinolyncarbonyl) amino]ethoxy]phenyl]sulfonyl]amino]benzoic acid Sodium hydride (0.1 g, 2.3 mmol, 60% dispersion in mineral oil) was added to DMF (5 ml) and stirred at room temperature 10 minutes. A solution of N-(2-hydroxyethyl) 2-quinolinecarboxamide (0.21 g, 0.99 mmol) in DMF (1 ml) was added followed by a solution of the product of Example 2 (0.3 g, 0.98 mmol) in DMF (1 ml). After 3 hours, the solution was diluted with ethyl acetate and a sticky solid was filtered off. The solid was taken up in water, and the solution was acidified with 1N HCl. Filtration of the resulting precipitate gave 0.29 g (49% yield) of white powder. $^1$NMR (DMSO-d$_6$): δ 1.9 (s, CH3), 3.17 (s, CH3), 3.75 (m, CH2), 4.23 (m, CH2), 7.1 (d, 2 Ar H) 7.29–7.30 (m, 2 Ar H), 7.52–7.58 (m, 2 Ar H), 7.71–7.76 (t, 1 Ar H), 7.86–7.91 (t, 1 Ar H), 8.0–8.2 (m, 3 Ar H), 8.57–8.60 (d, 1 Ar H), 8.9 (s, 1 Ar H) 9.1 (br t, NH), 12.9 (s, OH). Electrospray Mass Spec: m/z 520.2 (M+H)$^+$.

EXAMPLE 4

Quinoline-2-carboxylic acid (2-{4-[(2-hydroxycarbamoyl-6-methyl-phenyl)-methyl-sulfamoyl]-phenoxy}-ethyl)-amide The product of Example 3 (0.17 g, 0.33 mmol) was dissolved in DMF (5 ml). 1-hydroxybenzotriazole (HOBT) (0.1 g, 0.8 mmol), 1-(3-dimethylaminopropyl)-3-ethylcarbodiimide hydrochloride (0.17 g, 0.92 mmol), hydroxylamine hydrochloride (0.18 g, 2.64 mmol) and finally triethylamine (0.46 ml, 3.3 mmol) were added sequentially to the solution and allowed to stir at room temperature. After 15 hours, ethyl acetate was added and the resulting precipitate filtered and triturated from ethyl ether to give 0.99 g (36% yield) of the hydroxamic acid as a white powder. MP 114–121° C.; $^1$H NMR (DMSO-d$_6$): δ 2.1 (s, CH3), 3.14 (s, CH3), 3.62 (m, CH2), 3.8 (m, CH2), 7.1 (d, 2 Ar H) 7.29–7.30 (m, 2 Ar H), 7.52–7.58 (d, 1 Ar H), 7.71–7.76 (m, 3 Ar H), 7.86–7.91 (t, 1 Ar H), 8.0–8.2 (m, 3 Ar H), 8.57–8.60 (d, 1 Ar H), 8.89 (s, NH) 9.1 (br t, NH), 11.0 (s, OH). Electrospray Mass Spec: m/z 535.2 (M+H)$^+$.

EXAMPLE 5

2-[(4-{3-[(Benzofuran-2-carbonyl)-amino]-propoxy}-benzenesulfonyl)-methyl-amino]-3methyl-benzoic acid The product of Example 2 (0.442 g, 1.37 mmol) was coupled to N-(3-hydroxypropyl)-1-benzofuran-2-carboxamide (0.3 g, 1.37 mmol) using the procedure of Example 3 to provide 0.37 g (53% yield) of an off white powder. MP 184–186° C.; $^1$H NMR (DMSO-d$_6$): δ 1.9 (s, CH3), 2.04 (t, CH2), 3.16 (s, CH3), 3.46 (q, CH2), 4.0 (t, CH2), 7.01 (d, 2 Ar H) 7.30–7.78 (m, 10 Ar H), 8.56 (t, NH), 12.4 (br s, OH). Electrospray Mass Spec: m/z 523.2 (M+H)$^+$.

EXAMPLE 6

Benzofuran-2-arboxylic acid (3-{4-[(2-hydroycarbamoyl-6-methyl-phenyl)methyl-sulfamoyl]-phenoxy}-propyl)-amide The product of Example 5 (0.172 g, 0.33 mmol) was converted to the hydroxamic acid using the procedure of Example 4 to provide 0.073 g (41% yield) of a white solid. MP 148–150° C.; $^1$H NMR (DMSO-d$_6$): δ 2.1 (s, CH3), 2.04 (t, CH2), 3.06 (s, CH3), 3.39 (q, CH2), 4.0 (t, CH2), 7.01 (d, 2 Ar H) 7.30–7.78 (m, 10 Ar H), 8.85 (t, NH), 8.89 (s, NH), 11.0 (s, OH). Electrospray Mass Spec: 538.1 m/z (M+H)$^+$.

EXAMPLE 7

2-[(4-{4-[(Benzofuran-2-carbonyl)-amino]-butoxy}-benzenesulfonyl)-methyl-amino]-3-methyl-benzoic acid The product of Example 2 (0.40 g, 1.24 mmol) was coupled to N-(4-hydroxybutyl)-1-benzofuran-2-carboxamide, prepared according to Example 17, (0.29 g, 1.24 mmol) using the procedure of Example 3 to provide 0.34 g (51% yield) of an off white powder. MP>200° C.; $^1$H NMR (DMSO-d$_6$): δ 1.35–1.62 (m, CH2, CH2), 1.9 (s, CH3), 3.20 (s, CH3), 3.32–3.41 (m, CH2, CH2), 7.0–7.1 (m, 4 Ar H), 7.35 (t, 1 Ar H), 7.45 (t, 1 Ar H), 7.54 (s, 1 Ar H), 7.65 (d, 1 Ar H), 7.77 (d, 1 Ar H), 7.92 (m, 3 Ar H) 8.8 (t, NH), Electrospray Mass Spec: m/z 537.2 (M+H)$^+$.

EXAMPLE 8

Benzofuran-2-carboxylic acid (4-{4-[(2-hydroxycarbamoyl-6-methyl-phenyl)-methyl-sulfamoyl]-phenoxy}-butyl)-amide The product of Example 7 (0.2 g, 0.37 mmol) was converted to the hydroxamic acid using the procedure of Example 4 to provide 0.063 g (31% yield) of a white solid. MP 131–134° C.; $^1$H NMR (DMSO-d$_6$): δ 1.7–1.8 (m, CH2, CH2), 1.9 (s, CH3), 3.20 (s, CH3), 3.34–3.41 (m, CH2, CH2), 7.0–7.1 (d, 1 Ar H), 7.19 (d, 1 Ar H), 7.30–7.78 (m, 9 Ar H), 7.9 (d, 1 Ar H), 8.79 (t, NH), 8.88 (br s, NH), 10.99 (s, OH). Electrospray Mass Spec: 552.2 m/z (M+H)$^+$.

EXAMPLE 9

2-[(4-{3-[(1H-Indole-2-carbonyl)-amino]-propoxy}-benzenesulfonyl)-methyl-amino]-3-methyl-benzoic acid The product of Example 2 (0.27 g, 0.83 mmol) was coupled to N-(3-hydroxypropyl)-1H-indole-2-carboxamide, prepared according to Example 18, (0.20 g, 0.91 mmol) using the procedure of Example 3 to provide 0.4 g (91% yield) of yellow solid powder. MP 199° C.; $^1$H NMR (DMSO-d$_6$): δ 1.9 (s, CH3), 2.0–2.1 (m, CH2), 3.20 (s, CH3), 3.32–3.51 (m, CH2, CH2), 6.8–7.2 (m, 8 Ar H), 7.36 (d, 1 Ar H), 7.58 (d, 1 Ar H), 7.78 (d, 1 Ar H), 7.93 (s, 1 NH), 8.52 (s, NH), 12.0 (s, OH). Electrospray Mass Spec: m/z 522.2 (M+H)$^+$.

EXAMPLE 10

1H-Indole-2-carboxylic acid (3-{4-[(2-hydroxycarbamoyl-6-methyl-phenyl)-methyl-sulfamoyl]-phenoxy}-propyl)-amide The product of Example 9 (0.2 g, 0.38 mmol) was converted to the hydroxamic acid using the procedure of Example 4 to provide 0.112 g (55% yield) of a white solid. MP 144–146° C.; $^1$H NMR (DMSO-d$_6$): δ 1.9 (s, CH3), 1.35–1.62 (m, CH2), 3.20 (s, CH3), 3.46–3.51 (m, CH2, CH2), 7.0–7.19 (m, 5 Ar H), 7.28–7.40 (m, 3 Ar H), 7.43–7.55 (m, 2 Ar H), 7.7 (d, 2 Ar H), 8.58 (t, NH), 8.9 (br s, NH), 10.9 (s, NH), 11.7 (s, OH). Electrospray Mass Spec: m/z 537.1 (M+H)$^+$.

EXAMPLE 11

2-[(4-{3-[(Benzo[b]thiophene-2-carbonyl)-amino]-ethoxy}-benzenesulfonyl)-benzenesulfonyl)-methyl-amino]-3-methyl-benzoic acid The product of Example 2 (0.15 g, 0.846 mmol) was coupled to N-(2-hydroxyethyl)-1-benzothiophene-2-carboxamide, prepared according to Example 19, (0.11 g, 0.51 mmol) using the procedure of Example 3 to provide 0.26 g (80% yield) of yellow solid. MP 250° C.; $^1$H NMR (DMSO-d$_6$): δ 1.9 (s, CH3), 3.20 (s, CH3), 3.6 (m,CH2), 4.1 (m, CH2), 7.0–7.17 (m, 4 Ar H), 7.34–7.37 (m, 2Ar H), 7.81–7.95 (m, 6 Ar H), 8.52 (s, NH). Electrospray Mass Spec: m/z 525.0 (M+H)$^+$.

EXAMPLE 12

Benzo[b]thiophene-2-carboxylic acid (2-{4-[(2-hydroxycarbamoyl-6-methyl-phenyl)-methyl-sulfamoyl]-phenoxyl}-ethyl)-amide The product of Example 11 (0.2 g, 0.38 mmol) was converted to the hydroxamic acid using the procedure of Example 4 to provide 0.048 g (25% yield) of a white solid. MP 169–171° C. $^1$H NMR (DMSO-d$_6$): δ 8 1.35–1.62 (m, CH2), 1.9 (s, CH3), 3.20 (s, CH3), 3.46–3.51 (m, CH2, CH2), 7.0–7.95 (m, 11 Ar H), 8.0 (s, 1 Ar H), 8.58 (t, N H), 9.0 (br s, NH), 10.9 (s, OH). Electrospray Mass Spec: m/z 540.2 (M+H)$^+$.

EXAMPLE 13

2-[[(4-{3-[(1,3-Benzodioxol-5-ylcarbonyl)amino] propoxy}phenyl)sulfonyl](methyl)amino]-3-methyl benzoic acid The product of Example 2 (0.30 g, 0.92 mmol) was coupled to N-(3-hydroxypropyl)-1,3-benzodioxole-5-carboxamide, prepared according to Example 20, (0.205 g, 0.92 mmol) using the procedure of Example 3 to provide 0.23 g (49% yield) of yellow solid. MP 120° C.; $^1$H NMR (DMSO-d$_6$): δ 1.63 (m, CH2) 1.9 (s, CH3), 3.20 (s, CH3), 3.6 (m, CH2), 4.1 (m, CH2), 6.07 (s, CH2), 6.9–7.1 (m, 5 Ar H), 7.3–7.5 (m, 3 Ar H), 7.88–7.94 (m, 2 Ar H), 8.52 (br s, NH). Electrospray Mass Spec: m/z 527.2 (M+H)$^+$.

EXAMPLE 14

N-{3-[4({2-[(Hydroxyamino)carbonyl]-6-dimethylaniline}sulfonyl)phenoxy]propyl}-1,3-benzodioxole-5-carboxamide The product of Example 13 (0.2 g, 0.38 mmol) was converted to the hydroxamic acid using the procedure of Example 4 to provide 0.102 g (50% yield) of a white solid. MP 102–112° C.; $^1$H NMR (DMSO-d$_6$): δ 1.63 (m, CH2) 1.9 (s, CH3), 3.20 (s, CH3), 3.6 (m, CH2), 4.1 (m, CH2), 6.08 (s, CH2), 6.96–6.99 (m, Ar H), 7.02–7.09 (m, 3 Ar H), 7.30–7.45 (, 3 Ar H), 7.52–7.58 (m, 2 Ar H), 7.69–7.72 (d,d, 1 Ar H), 7.82–7.85 (d, 1 Ar H), 8.25 (m, NH), 8.40 (br s, NH), 10.9 (br s, OH). Electrospray Mass Spec: m/z 542.1 (M+H)$^+$.

EXAMPLE 15

2-[[(4-{4-[(1,3-Benzodioxol-5-ylcarbonyl)amino] butoxy}phenyl)sulfonyl](methyl)amino]-3-methyl benzoic acid The product of Example 2 (0.30 g, 0.92 mmol) was coupled to N-(4hydroxybutyl)-1,3-benzodioxole-5-carboxamide, prepared according to Example 21, (0.23 g, 0.96 mmol) using the procedure of Example 3 to provide 0.30 g (60% yield) of yellow solid. MP 110° C.; $^1$H NMR (DMSO-d$_6$): δ 1.66–1.80 (m,CH2, CH2)1.89 (s, CH3), 3.1 (s, CH3), 3.39–3.45 (m, CH2), 4.08 (t, CH2), 6.08 (s, CH2), 6.9 (d, 1 Ar H), 7.04–7.08 (m, 2 Ar H), 7.33–7.45 (m, 5 Ar H), 7.53–7.58 (m, 2 Ar H), 8.39 (t, NH), 12.8 (s, OH). Electrospray Mass Spec: m/z 541.2 (M+H)$^+$.

EXAMPLE 16

N-{4-[4-({2-[(Hydroxyamino)carbonyl]-6-dimethylanilino}sulfonyl)phenoxy]butyl}-1,3-benzodioxole-5-carboxamide The product of Example 15 (0.15 g, 0.28 mmol) was converted to the hydroxamic acid using the procedure of Example 4 to provide 0.092 g (40% yield) of a white solid. MP 117–121° C.; $^1$H NMR (DMSO-d$_6$): δ 1.66–1.80 (m,CH2, CH2)1.89 (s, CH3), 3.1 (s, CH3), 3.39–3.45 (m, CH2), 4.08 (t, CH2), 6.08 (s, CH2), 6.96 (d, 1 Ar H), 7.04–7.08 (d,d 2 Ar H), 7.17–7.19 (d,d 1 Ar H), 7.28–7.38 (m, 3 Ar H), 7.45 (d,d 1 Ar H), 7.68–7.80 (m, 2 Ar H), 7.95 (s, 1 Ar H), 8.32 (t, NH), 8.88 (br s, NH), 11.0 (s, OH). Electrospray Mass Spec: m/z 540.2 (M+H)$^+$.

EXAMPLE 17

N-(4-Hydroxybutyl)-1-benzofuran-2-carboxamide

2-Benzofurancarboxylic acid (5.0 g, 30.8 mmol) and 4-amino-1-butanol (3.4 ml, 37 mmol) were dissolved in DMF (45 ml). 1-hydroxybenzotriazole (5.0 g, 37 mmol), 1-(3-dimethylaminopropyl)-3-ethylcarbodiimide hydrochloride (7.7 g, 40 mmol), and diisopropylethylamine (10.7 ml, 61.7 mmol) were added sequentially to the solution and allowed to stir at room temperature overnight. After removing excess solvent in vacuo, the residue was taken up in water and the product was extracted into dichloromethane. The organics were combined, washed with brine, dried over Na$_2$SO$_4$, and solvent removed in vacuo to give a solid which was purified by column chromatography (100% ethyl acetate) to give 3.5 g (50% yield) of a white solid. $^1$H NMR (DMSO-d$_6$): δ 1.35–1.62 (m, CH2, CH2), 3.29 (q, CH2), 3.41 (q, CH2), 4.3 (t, NH), 7.78 (d, 1 Ar H), 7.63 (d, 1 Ar H), 7.51 (s, 1 Ar H), 7.46 (t, 1 Ar H), 7.35 (t, 1 Ar H), 8.71 (t, NH) Electrospray Mass Spec: m/z 234.2 (M+H)$^+$.

EXAMPLE 18

N-(3-Hydroxypropyl)-1H-indole-2-carboxamide

1H Indole-2-carboxylic acid (5.0 g, 31 mmol) and 3-amino-1-propanol (2.2 ml, 40.3 mmol) were coupled according to the procedure of Example 17 to 5.46 g (80% yield) of an off-white solid. MP 152–156° C.; $^1$H NMR (DMSO-d$_6$): δ 1.6–1.7 (m, CH2),3.31–3.37 (q, CH2), 3.41–3.51 (q, CH2), 4.52 (t, NH), 7.0–7.19 (m, 3 Ar H), 7.40 (d, 1 Ar H), 7.58 (d, 1 Ar H), 8.46 (t, NH), 11.9 (s, NH) Electrospray Mass Spec: m/z 217.2 (M+H)$^+$.

EXAMPLE 19

N-(2-Hydroxyethyl)-1-benzothiophene-2-carboxamide

2-Benzothiophenecarboxylic acid (3.0 g, 16.8 mmol) and ethanolamine (1.21 ml, 20 mmol) were coupled according to the procedure of Example 17 to 2.7 g (73% yield) of an off-white solid. $^1$H NMR (DMSO-d$_6$): δ 3.3 (m, CH2), 3.5 (q, CH2), 4.79 (t, NH), 7.1–7.4 (m, 2 Ar H), 7.90 (m, 1 Ar H), 7.95 (m, 1 Ar H), 8.09 (s, 1 Ar H), 8.89 (t, NH) Electrospray Mass Spec: m/z 222.2 (M+H)$^+$.

EXAMPLE 20

N-(3-Hydroxyproyl)-1,3-benzodioxole-5-carboxamide 1,3-Benzodioxole-5-carboxylic acid (2.0 g, 12.0 mmol) and 3-amino-1propanol (0.8 ml, 15.6 mmol) were coupled according to the procedure of Example 17 to 1.74 g (65% yield) of a white solid. MP 112–113° C.; $^1$H NMR (DMSO-d$_6$): δ 1.65 (m, CH2), 3.27 (m, CH2), 3.42 (m, CH2), 4.45 (t, NH), 6.0 (s, CH2), 6.98 (d, 1 Ar H), 7.37 (d, 1 Ar H), 7.4 (d-d, 1 Ar H), 8.28 (t, NH) Electrospray Mass Spec: m/z 224.2 (M+H)$^+$.

EXAMPLE 21

N-(4-Hydroxybutyl)-1,3-benzodioxole-5-carboxamide 1,3-Benzodioxole-5-carboxylic acid (2.0 g, 12.0 mmol) and 4-amino-1-butanol (1.4 ml, 15.6 mmol) were coupled according to the procedure of Example 17 to 2.1 g (75% yield) of a pale yellow solid. MP 95–98° C.; $^1$H NMR (DMSO-d$_6$): δ 1.38–1.65 (m, CH2, CH2), 3.31 (q, CH2), 3.39 (q, CH2), 4.39 (t, NH), 6.08 (s, CH2), 6.98 (d, 1 Ar H), 7.37 (d, 1 Ar H), 7.4 (d-d, 1 Ar H), 8.27 (t, NH) Electrospray Mass Spec: m/z 238.2 (M+H)$^+$.

EXAMPLE 22

N-(2-Hydroxyethyl) 2-quinolinecarboxamide

To a solution of quinaldic acid (5.0 g, 28.87 mmol), 1-(3dimethylaminopropyl)-3-ethylcarbodiimide hydrochloride (5.5 g, 28.87 mmol), and 1-hydroxybenzotriazole (5.1 g, 37.49 mmol) in DMF (60 mL) at 0° C. was added ethanolamine (1.74 mL, 28.87 mmol) and 4-methylmorpholine (4.76 mL, 43.31 mmol). The reaction was stirred at 0° C. for an additional 10 minutes and then warmed to room temperature and stirred for 2 hours. The reaction mixture was then diluted with ethyl acetate, washed 3 times with H$_2$O, once with NaHCO$_3$ (sat), once with brine, dried over MgSO$_4$, and concentrated in vacuo to provide 1.5 g (24% yield) of a pale yellow solid. Electrospray Mass Spec: m/z 216.8 (M+H)$^+$.

EXAMPLE 23

N-(3-Hydroxypropyl)-1-benzofuran-2-carboxamide

2-Benzofunrancarboxylic acid (5.0 g, 30.8 mmol) and 3-amino-1-propanol (2.83 ml, 37 mmol) were coupled according to the procedure of example 22 to provide 1.39 g (17.2% yield) of the desired product as a yellow solid. Electrospray Mass Spec: m/z 219.8 (M+H)$^+$.

EXAMPLE 24

N-(3-Hydroxypropylo-1-benzothiophene-2-carboxamide

2-Benzothiophenecarboxylic acid (5.0 g, 28.05 mmol) and 3-amino-1-propanol (2.57 ml, 33.66 mmol) were coupled according to the procedure of Example 22 to provide 3.45 g (52.3% yield) of the desired product as an orange solid. Electrospray Mass Spec: m/z 235.9 (M+H)$^+$.

EXAMPLE 25

N-(2-Hydroxypropyl)-1-benzofuran-2-carboxamide

2-Benzofurancarboxylic acid (1.0 g, 6.16 mmol) and ethanolamine (0.37 ml, 6.16 mmol) were coupled according to the procedure of Example 22 to provide 0.55 g (43% yield) of the desired product as a yellow solid. MP 90–91° C. Electrospray Mass Spec: m/z 205.8 (M+H)$^+$.

EXAMPLE 26

2-[[(4-{3-[(1-Benzothiophene-2-ylcarbonyl)amino] propoxy}phenyl)sulfonyl](methyl)amino]-3-methyl benzoic acid The product of Example 2 (0.5 g, 1.58 mmol) was coupled to N-(3-hydroxypropyl)-1-benzothiophene-2-carboxamide (1.26 g, 5.37 mmol) using the procedure of Example 3 to provide 0.16 g (19% yield) of an off white solid. Electrospray Mass Spec: m/z 539.3 (M+H)$^+$.

EXAMPLE 27

N-{3-[4-({2-[(Hydroxyamino)carbonyl]-6dimethylanilino}-sulfonyl)phenoxy]propyl}-1-benzothiophene-2-carboxamide The product of Example 26 (0.16 g, 0.30 mmol) was converted to the hydroxamic acid using the procedure of Example 4 to provide 0.1 g (60% yield) as a pink foam. MP 100–105° C. Electrospray Mass Spec: m/z 554.0 (M+M)$^+$.

EXAMPLE 28

2-(4-Fluoro-benzenesulfonylamino)-3,5-dimethyl-benzoic acid methyl ester

To a solution of 2.00 g (0.011 mmol) of methyl 3,5-dimethylanthranilic acid in 10.0 mL of pyridine was added 2.17 (0.011 mmol) of 4-fluorobenzenesulfonyl chloride. The reaction mixture was stirred for 24 h at room temperature and then diluted with chloroform and washed with 5% HCl solution and water. The organic layer was then dried over MgSO$_4$, filtered and concentrated in vacuo. The residue was triturated with ether-hexanes and the resulting solid was filtered and dried to provide 3.09 g (82%) of the desired product as a white solid. Electrospray Mass Spec: m/z 338.3 (M+H)$^+$.

EXAMPLE 29

2-[Benzyl-(4-fluoro-benzenesulfonyl)-amino]-3,5-dimethyl-benzoic acid methyl ester To a solution of 1.00 g (2.86 mmol) of the product of Example 28 in 10 mL of DMF was added 0.14 g (3.57 mmol) of 60% sodium hydride. The resulting mixture was stirred for 30 min at room temperature and then 0.42 mL (3.57 mmol) of benzyl bromide was added. This reaction mixture was stirred overnight at room temperature, poured into water and then extracted with ether. The combined organics were washed with water and brine, dried over MgSO$_4$, filtered and concentrated in vacuo to provide a white solid which was recrystallized from ethyl acetate (EtOAc)/Hexanes to provide 1.084 g (85%) of the desired product as a white solid. Electrospray Mass Spec: m/z 428.3 (M+H)$^+$.

EXAMPLE 30

2-[[(4-{2-[(Benzofuran-2-carbonyl)-amino]ethoxy}benzenesulfonyl]benzylamino]-3,5-dimethyl-benzoic acid Sodium hydride (0.240 g, 5.99 mmol, 60% dispersion in mineral oil) was added to DMF (8 ml) and cooled to 0° C. A solution of N-(2-hydroxypropyl)-1-benzofuran-2-carboxamide (0.6 g, 2.92 mmol) in DMF (1.5 ml) was added and allowed to stir for 10 min at 0° C. and then for 15 min at rt. The product of Example 29 (0.383 g, 0.87 mmol) was then added in one portion and the reaction was allowed to stir overnight. The reaction was then quenched with water, extracted with EtOAc, washed with water, brine, dried over $MgSO_4$, and concentrated in vacuo to provide an oil which was chromatographed using hexane to 2/1 hexane/EtOAc as eluant to provide the product as a mixture of esters which was used directly in the next reaction. The mixture of esters (233 mg) was dissolved in $THF:MeOH:H_2O$ (1.2mL:0.7 mL) and LiOH (13.7 mg, 0.32 mmol) was added. The reaction was heated at reflux overnight. The reaction was cooled to rt, quenched with 6M HCl and extracted with $CH_2Cl_2$. The organics were washed with brine, dried over $Na_2SO_4$, concentrated in vacuo to provide an oil which was chromatographed using hexane to 9/1 $CH_2Cl_2$/MeOH as eluant to provide 80 mg (44% yield) of the product acid. Electrospray Mass Spec: m/z 597.2 (M–H)–.

EXAMPLE 31

Benzofuran-2-carboxylic acid (2-{4-[benzyl-(2-hydroxycarbamoyl-4,6-dimethyl-phenyl)-sulfamoyl]-phenoxy}-ethyl)-amide DMF (0.0021 mL, 0.26 mmol) was added to oxallyl chloride (0.13 ml, 0.267 mmol, 2M in $CH_2Cl_2$) at 0° C. This mixture was allowed to warm to rt and stir for 45 min. To this suspension was added a solution of the product from Example 30 (80 mg, 0.13 mmol) in DMF (1 mL). The solution of the acid chloride was then stirred for 4 hours.

In a separate flask, 0.27 mL (1.95 mmol) of triethylamine was added to 0° C. mixture of 0.09 g (1.3 mmol) of hydroxylamine hydrochloride in 1.49 mL of THF and 0.43 mL of water. After this mixture had stirred for 15 min at 0° C., the acid chloride solution was added to it in one portion and the resulting solution was allowed to warm to room temperature with stirring overnight. The reaction mixture was then acidified to pH3 with 10% HCl and extracted with EtOAc. The combined organic layers were dried over $Na_2SO_4$, filtered and concentrated in vacuo. The crude residue was chroamtographed using 95/5 $CH_2Cl_2$/MeOH as eluant to provide 0.020 g (25%) of the desired hydroxamic acid as a white solid. Electrospray Mass Spec: m/z 612.2 (M–H)–.

Pharmacology

Procedures for Measuring MMP-1, MMP-9, and MMP-13 Inhibition

These assays are based on the cleavage of a thiopeptide substrates such as Ac-Pro-Leu-Gly(2-mercapto-4-methyl-pentanoyl)-Leu-Gly-OEt by the matrix metalloproteinases MMP-1, MMP-13 (collagenases) or MMP-9 (gelatinase), which results in the release of a substrate product that reacts calorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM $CaCl_2$) before use. The stock of enzyme is diluted with assay buffer (50 mM HEPES, pH 7.5, 5 mM $CaCl_2$, 0.02% Brij) to the desired final concentration. The assay buffer, enzyme, vehicle or inhibitor, and DTNB/substrate are added in this order to a 96 well plate (total reaction volume of 200 $\mu l$) and the increase in color is monitored spectrophotometrically for 5 minutes at 405 nm on a plate reader and the increase in color over time is plotted as a linear line.

Alternatively, a fluorescent peptide substrate is used. In this assay, the peptide substrate contains a fluorescent group and a quenching group. Upon cleavage of the substrate by an MMP, the fluorescence that is generated is quantitated on the fluorescence plate reader. The assay is run in HCBC assay buffer (5 mM HEPES, pH 7.0, 5 mM $Ca^{+2}$, 0.02% Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide assays, the slope of the line is calculated and represents the reaction rate. The linearity of the reaction rate is confirmed ($r^2>0.85$). The mean (x±sem) of the control rate is calculated and compared for statistical significance (p<0.05) with drug-treated rates using Dunnett's multiple comparison test. Dose-response relationships can be generated using multiple doses of drug and $IC_{50}$ values with 95% CI are estimated using linear regression.

Procedure for Measuring TACE Inhibition

Using 96-well black microtiter plates, each well receives a solution composed of 10 $\mu L$ tumor necrosis factor-alpa converting enzyme (TACE; Immunex, final concentration 1 $\mu g/mL$), 70 $\mu L$ Tris buffer, pH 7.4 containing 10% glycerol (final concentration 10 mM), and 10 $\mu L$ of test compound solution in DMSO (final concentration 1 $\mu M$, DMSO concentration <1%) and incubated for 10 minutes at room temperature. The reaction is initiated by addition of a fluorescent peptidyl substrate (final concentration 100 $\mu M$) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2>0.85$). The mean (x±sem) of the control rate is calculated and compared for statistical significance (p<0.05) with drug-treated rates using Dunnett's multiple comparison test. Dose-response relationships can be generate using multiple doses of drug and $IC_{50}$ values with 95% CI are estimated using linear regression.

Results of the above in-vitro matrix metalloproteinase inhibition and TACE inhibition pharmacological assays are given in Table 1 below. Biological Data:

| Exampl | MMP-1[a] | MMP-9[a] | MMP-13[a] | TACE[b] |
|---|---|---|---|---|
| 4 | 4244 | 337 | 73 | 19.9 |
| 6 | 5450 | 510 | 4.9 | 21.3 |
| 8 | 5122 | 84 | 467 | 43.6 |
| 10 | 5642 | 305 | 178 | 35.7 |
| 12 | >10 μM | 914 | 595 | 15.2 |
| 14 | 1481 | 63.6 | 110 | 42.1 |
| 16 | 999 | 55.7 | 83.5 | 27.4 |
| 27 | 30 μM | 1390 | 43 | 22.0 |
| 31 | 10 μM | 945 | 17.1 | 18.9 |

[a]$IC_{50}$ (nM)
[b]% inhibition @1 μM

Compounds of this invention are shown to inhibit the enzymes MMP-1, MMP-9, MMP-13, and TACE and are therefore useful in the treatment of conditions resulting from overexpression or excess activation of MMPs and TACE. Such diseases are, for example, atherosclerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, and periodontal disease. Compounds of the present invention are also believed to be useful for the treatment of age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization or corneal graft rejection. In addition, compounds of the present invention are believed to be useful for the treatment of graft rejection, cachexia, anorexia, inflammation, fever, insulin resistance, septic shock, congestive heart failure, inflammatory disease of the central nervous system, or HIV infection.

What is claimed is:

1. A compound of formula I

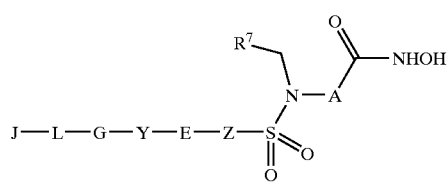

where the hydroxamic acid moiety and the sulfonamido moiety are bonded to adjacent carbons of group A wherein:
A is aryl;
Z is aryl;
E and G are independently $CH_2$, $NR^5$, O, S or a bond;
Y is cycloalkyl, —$C_1$–$C_5$-perfluoroalkyl, alkyl, alkenyl, alkynyl, or alkylaryl;
J is quinolinyl or indolyl;
$R^5$ and $R^6$ are independently H, aryl, heteroaryl, cycloalkyl, cycloheteroalkyl, —$C_1$–$C_4$-perfluoroalkyl, alkyl, alkenyl, or alkynyl;

$R^7$ is hydrogen, alkyl, alkenyl, alkynyl, aryl, heteroaryl, cycloalkyl or 3–6 membered cycloheteroalkyl; or $R^7CH_2$—N—A— can form a non-aromatic 1,2-benzofused 7–10 membered heterocyclic ring optionally containing an additional heteroatom selected from the group consisting of O, S and N wherein said heterocyclic ring may be optionally fused to another benzene ring;

L is —C(O)—, $S(O)_y$, —$NR^5C(O)NR^6$—, —$NR^5C(O)O$—, —$OC(O)NR^5$—, —SC(O)—, —C(O)S—, —$NR^5C(O)$—, —$C(O)NR^5$—, —$SC(O)NR^5$, —$NR^5C(O)S$—, or —OC(O)O—;

y is 1 or 2;

or the pharmaceutically acceptable salts, optical isomers or diastereomers thereof.

2. The compound according to claim 1 wherein:

A is aryl optionally substituted by one or more of $R^1$, $R^2$, $R^3$ and $R^4$;

Z is aryl optionally substituted by one or more of $R^{10}$, $R^{11}$, $R^{12}$ and $R^{13}$;

$R^1$, $R^2$, $R^3$, $R^4$, $R^{10}$, $R^{11}$, $R^{12}$, $R^{13}$, $R^{14}$, $R^{15}$, $R^{16}$, $R^{17}$, $R^{20}$, $R^{21}$, $R^{22}$, $R^{23}$, $R^{25}$, $R^{26}$, $R^{27}$, $R^{28}$, $R^{29}$, $R^{30}$ and $R^{31}$ are independently —H, —$COR^5$, —F, —Br, —Cl, —I, $C(O)NR^5OR^6$, —CN, —$OR^5$, —$C_1$–$C_4$-perfluoroalkyl, —$S(O)_xR^5$, —$OPO(OR^5)OR^6$, —$PO(OR^6)R^5$, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R^5)SO_2R^6$, —$NR^5CONR^5R^6NR^5C(=NR^6)NR^5R^{6,}$ 3–6 membered cycloheteroalkyl, aryl, heteroaryl, biphenyl, —$SO_2NHCOR^{18}$, —$CONHSO_2R^{18}$, -tetrazol-5-yl, —$SO_2NHCN$, —$SO_2NHCONR^5R^6$ or straight chain or branched —$C_1$–$C_6$ alkyl, —$C_2$–$C_6$-alkenyl, or —$C_2$–$C_6$-alkynyl, or —$C_3$–$C_6$-cycloalkyl, each optionally substituted with —$COR^5$, —CN, —$C_2$–$C_6$ alkenyl, —$C_2$–$C_6$ alkynyl, —$OR^5$, —$C_1$–$C_4$-perfluoroalkyl, —$S(O)_xR^5$, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R^5)SO_2R^6$, —$NR^5CONR^5R^6$, —$C_3$–$C_6$ cycloalkyl, 3–6 membered cycloheteroalkyl, aryl, heteroaryl, biphenyl, —$SO_2NHCOR^{18}$, —$CONHSO_2R^{18}$; —$PO(OR^5)OR^6$, —$PO(OR^6)R^5$, -tetrazol-5-yl, $C(O)NR^5OR^6$, —$NR^5C(=NR^6)NR^5R^6$, —$SO_2NHCONR^5R^6$ or —$SO_2NHCN$; or when any of $R^1$ and $R^2$, $R^{10}$ and $R^{11}$ or $R^{14}$ and $R^{15}$ are on adjacent carbons of A, J or Z respectively, then each pair of $R^1$ and $R^2$, $R^{10}$ and $R^{11}$ or $R^{14}$ and $R^{15}$ together with the carbons to which they are attached can form a 5 to 7 membered saturated or unsaturated heterocyclic ring, a 5–6 membered heteroaryl ring, or a 5 to 7 membered saturated or unsaturated carbocyclic ring;

x is 0–2;

E and G are independently $CH_2$, $NR^5$, O, S or a bond:

Y is —$C_3$–$C_6$-cycloalkyl, —$C_1$–$C_5$-perfluoroalkyl, straight chain or branched —$C_1$–$C_6$ alkyl, straight or branched chain —$C_2$–$C_6$-alkenyl, straight or branched chain $C_2$–$C_6$-alkynyl or alkylaryl, optionally substituted with $R^{20}$, $R^{21}$, $R^{22}$, or $R^{23}$;

J is quinolenyl or indonyl, optionally substituted with $R^{14}$, $R^{15}$, $R^{16}$, or $R_{17}$;

$R^5$ and $R^6$ are independently H, aryl, heteroaryl, —$C_3$–$C_6$-cycloalkyl, —$C_3$–$C_6$–cycloheteroalkyl, —$C_1$–$C_4$-perfluoroalkyl, or straight chain or branched —$C_1$–$C_6$ alkyl, —$C_2$–$C_6$-alkenyl, or —$C_2$–$C_6$-alkynyl, each optionally substituted with —OH, —COR$^8$, —CN, —C(O)NR$^8$OR$^9$, —C$_2$–C$_6$-alkenyl, —C$_2$–C$_6$-alkyenyl, —OR$^8$, —C$_1$–C$_4$-perfluoroalkyl, —S(O)$_x$R$^8$, —OPO(OR$^8$)OR$^9$, —PO(OR$^8$)R$^9$, —OC(O)NR$^8$R$^9$, —COOR$^8$, —CONR$^8$R$^9$, —SO$_3$H, —NR$^8$R$^9$, —NCOR$^8$R$^9$, —NR$^8$COOR$^9$, —SO$_2$NR$^8$R$^9$, —NO$_2$, —N(R$^8$)SO$_2$R$^9$, —NR$^8$CONR$^8$R$^9$, —C$_3$–C$_6$cycloalkyl, 3–6 membered cycloheteroalkyl, aryl, heteroaryl, —SO$_2$NHCOR$^{19}$, —CONHSO$_2$R$^{19}$, -tetrazol-5-yl, NR$^8$C(=NR$^9$)NR$^8$R$^9$, —SO$_2$NHCONR$^8$R$^9$, or —SO$_2$NHCN;

R$^7$ is hydrogen, straight chain or branched —C$_1$–C$_6$-alkyl, —C$_2$–C$_6$-alkenyl, or —C$_2$–C$_6$-alkynyl each optionally substituted with —OH, —COR$^5$, —CN, —C$_2$–C$_6$-alkenyl, —C$_2$–C$_6$-alkynyl, —OR$^5$, —C$_1$–C$_4$-perfluoroalkyl, —S(O)$_x$R$^5$, OPO(OR$^5$)OR$^6$, —PO(OR$^5$)R$^6$, —OC(O)NR$^5$R$^6$, —COOR$^5$, —CONR$^5$R$^6$, —SO$_3$H, —NR$^5$R$^6$, —NR$^5$COR$^6$, —NR$^5$COOR$^6$, —SO$_2$NR$^5$R$^6$, —NO$_2$, —N(R$^5$)SO$_2$R$^6$, —NR$^5$CONR$^5$R$^6$, —C$_3$–C$_6$ cycloalkyl, —C$_3$–C$_6$-cycloheteroalkyl, -aryl, heteroaryl, —SO$_2$NHCOR$^{32}$, —CONHSO$_2$R$^{32}$, -tetrazol-5-yl, —NR$^5$C(=NR6)NR$^5$R$_6$, —C(O)NR$^5$OR$^6$, —SO$_2$NHCONR$^5$R$^6$ or —SO$_2$NHCN; or R$^7$ is phenyl or naphthyl, optionally substituted by R$^{24}$, R$^{25}$, R$^{26}$ or R$^{27}$ or a 5 to 6 membered heteroaryl group optionally substituted by R$^{28}$, R$^{29}$, R$^{30}$ or R$^{31}$; or R$^7$ is C$_3$–C$_6$ cycloalkyl or 3–6 membered cycloheteroalkyl; or R$^7$CH$_2$—N—A— can form a non-aromatic 1,2-benzofuased 7–10 membered heterocyclic ring optionally containing an additional heteroatom selected from the group consisting of O, S and N wherein said heterocyclic ring may be optionally fused to another benzene ring;

R$^8$ and R$^9$ are independently H, aryl, heteroaryl, —C$_3$–C$_7$ cycloalkyl, 3 to 6 membered cycloheteroalkyl, —C$_1$–C$_4$-perfluoroalkyl, or straight chain or branched —C$_1$–C$_6$-alkyl, —C$_2$–C$_6$-alkenyl, or —C$_2$–C$_6$-alkynyl, each optionally substituted with hydroxy, alkoxy, aryloxy, —C$_1$–C$_4$-perfluoroalkyl, amino, mono- or di-C$_1$–C$_6$-alkylamino, carboxylic acid, carboalkoxy, carboaryloxy, nitro, cyano, carboxamido primary, mono- or di-C$_1$–C$_6$-alkylcarbamoyl;

R$^{18}$ and R$^{32}$ are independently aryl, heteroaryl, —C$_3$–C$_6$-cycloalkyl, —C$_3$–C$_6$-cycloheteroalkyl, —C$_1$–C$_4$-perfluoroalkyl, or straight chain or branched —C$_1$–C$_6$ alkyl, —C$_2$–C$_6$-alkenyl, or —C$_2$–C$_6$-alkynyl, each optionally substituted with —OH, —COR$^8$, —CN, —C(O)NR$^8$OR$^9$, —C$_2$–C$_6$-alkenyl, —C$_2$–C$_6$-alkynyl, —OR$^8$, —C$_1$–C$_4$-perfluoroalkyl, —S(O)$_x$R$^8$, —OPO(OR$^8$)OR$^9$, —PO(OR$^8$)R$^9$, —OC(O)NR$^8$R$^9$, —COOR$^8$, —CONR$^8$R$^9$, —SO$_3$H, —NR$^8$R$^9$, —NCOR$^8$R$^9$, —NR$^8$COOR$^9$, —SO$_2$NR$^8$R$^9$, —NO$_2$, —N(R$^8$)SO$_2$R$^9$, —NR$^8$CONR$^8$R$^9$, —C$_3$–C$_6$ cycloalkyl, 3–6 membered cycloheteroalkyl, aryl, heteroaryl, —SO$_2$NHCOR$^{19}$, —CONHSO$_2$R$^{19}$, -tetrazol-5-yl, NR$^8$C(=NR$^9$)NR$^8$R$^9$, —SO$_2$NHCONR$^8$R$^9$, or —SO$_2$NHCN;

R$^{19}$ is aryl heteroaryl, —C$_3$–C$_7$cycloalkyl, 3 to 6 membered cycloheteroalkyl, —C$_1$–C$_4$-perfluoroalkyl, or straight chain or branched —C$_1$–C$_6$-alkyl, —C$_2$–C$_6$-alkenyl, or —C$_2$–C$_6$-alkynyl, each optionally substituted with hydroxy, alkoxy, aryloxy, —C$_1$–C$_4$-perfluoroalkyl, amino, mono- or di-C$_1$–C$_6$-alkylamino, carboxylic acid, carboalkoxy, carboaryloxy, nitro, cyano, carboxamido primary, mono- or di-C$_1$–C$_6$-alkylcarbamoyl;

L is —(O)—, S(O)$_y$, —NR$^5$C(O)NR$^6$—, —NR$^5$C(O)O—, —OC(O)NR$^5$—, —SC(O)—, —C(O)S—, —NR$^5$C(O)—, —C(O)NR$^5$—, —SC(O)NR$^5$, —NR$^5$C(O)S—, or —OC(O)O—;

y is 1 or 2;

or the pharmaceutically acceptable salts, optical isomers or diastereomers thereof.

3. The compound according to claim 1 wherein E and G are independently selected from the group consisting of NH, O and S.

4. The compound according to claim 3 wherein E is O and G is NH.

5. The compound according to claim 1 wherein J is aryl or heteroaryl fused to a phenyl.

6. The compound according to claim 1 wherein J is quinolyl or indolyl optionally substituted by one or more of R$^{14}$, R$^{15}$, R$^{16}$ and R$^{17}$.

7. The compound according to claim 5 wherein J is selected from benzofuranyl, benzothienyl, quinolyl, benzodioxolyl or indolyl.

8. The compound according to claim 6 wherein J is selected from quinolin-2-yl or indol-2-yl.

9. The compound according to claim 1 wherein A is phenyl optionally substituted by H or straight or branched chain C$_1$–C$_6$ alkyl.

10. The compound according to claim 1 wherein Y is C$_1$–C$_6$ straight chain alkyl.

11. The compound according to claim 10 wherein Y is C$_2$–C$_3$ straight chain alkyl.

12. The compound of claim 1 wherein E and G are CH$_2$ and Y is straight chain or branched —C$_1$–C$_6$ alkyl.

13. The compound according to claim 1 wherein G is CH$_2$ and Y is C$_2$–C$_5$ -perfluoroalkyl, or straight chain or branched —C$_1$–C$_6$ alkyl.

14. The compound according to claim 1 wherein Z is phenyl.

15. The compound according to claim 1 wherein R$^7$ is H, straight or branched chain C$_1$–C$_6$ alkyl or phenyL.

16. The compound according to claim 1 wherein L is —CO—.

17. The compound according to claim 1 which is selected from the group consisting of:

Quinoline-2-carboxylic acid (2-{4-[(2-hydroxycarbamoyl-6-methyl-phenyl) -methyl-sulfamoyl]-phenoxy}-ethyl)-amide; and 1H-Indole-2-carboxylic acid (3-{4-[(2-hydroxycarbamoyl-6-methyl-phenyl)-methyl-sulfamoyl]-phenoxy}-propyl)-amide.

18. A pharmaceutical composition comprising a pharmaceutical carrier and a therapeutically effective amount of a matrix metalloproteinase inhibiting compound defined in claim 1.

* * * * *